(12) United States Patent
Leyser

(10) Patent No.: US 11,644,401 B2
(45) Date of Patent: May 9, 2023

(54) DEVICES AND METHODS FOR MEASURING VISCOELASTIC CHANGES OF A SAMPLE

(71) Applicant: enicor GmbH, Munich (DE)

(72) Inventor: Harald Leyser, Steinefrenz (DE)

(*) Notice: Subject to any disclaimer, the term of this patent is extended or adjusted under 35 U.S.C. 154(b) by 961 days.

(21) Appl. No.: 16/478,533

(22) PCT Filed: Jan. 26, 2017

(86) PCT No.: PCT/EP2017/051660
§ 371 (c)(1),
(2) Date: Jul. 17, 2019

(87) PCT Pub. No.: WO2018/137766
PCT Pub. Date: Aug. 2, 2018

(65) Prior Publication Data
US 2019/0331577 A1    Oct. 31, 2019

(51) Int. Cl.
| | | |
|---|---|---|
| *G01N 11/14* | (2006.01) | |
| *C12Q 1/56* | (2006.01) | |
| *G01N 33/49* | (2006.01) | |
| *G01N 33/86* | (2006.01) | |
| *G01N 11/00* | (2006.01) | |

(52) U.S. Cl.
CPC ........... *G01N 11/14* (2013.01); *C12Q 1/56* (2013.01); *G01N 33/4905* (2013.01); *G01N 33/86* (2013.01); *G01N 2011/002* (2013.01)

(58) Field of Classification Search
CPC .... G01N 11/14; G01N 33/4905; G01N 33/86; G01N 2011/002; G01N 2203/0094; G01N 27/22; C12Q 1/56
See application file for complete search history.

(56) References Cited

U.S. PATENT DOCUMENTS

| | | | |
|---|---|---|---|
| 3,714,815 A | 2/1973 | Hartert | |
| 4,148,216 A | 4/1979 | Do et al. | |
| 4,193,293 A | 3/1980 | Cavallari | |
| 5,777,215 A * | 7/1998 | Calatzis | G01N 33/4905 |
| | | | 73/64.41 |

(Continued)

FOREIGN PATENT DOCUMENTS

| | | | | |
|---|---|---|---|---|
| CH | 0545728 A1 * | 4/1992 | | G01N 11/16 |
| CN | 102272594 A | 12/2011 | | |

(Continued)

OTHER PUBLICATIONS

China National Intellectual Property Administration, Office Action, 8 pages, dated Jun. 15, 2020.

(Continued)

*Primary Examiner* — David Z Huang
(74) *Attorney, Agent, or Firm* — Sunstein LLP

(57) ABSTRACT

An apparatus is for use in viscoelastic analysis, for example in coagulation testing of sample liquids, such as blood and/or its elements. In the apparatus for use in viscoelastic analysis, the rotating means are provided below the cup, pin and cup receiving element. A capacitive detection means and temperature control devices may be used in the apparatus for use in viscoelastic analysis. A method of performing viscoelastic analysis, e.g. coagulation analysis, on a sample may use the devices and apparatuses.

22 Claims, 9 Drawing Sheets

(56) References Cited

U.S. PATENT DOCUMENTS

| | | | |
|---|---|---|---|
| 6,537,819 B2 | 3/2003 | Cohen et al. | |
| 2006/0027738 A1* | 2/2006 | Berting | G01D 5/241 |
| | | | 250/231.13 |
| 2010/0154520 A1* | 6/2010 | Schubert | B01L 3/52 |
| | | | 73/54.28 |
| 2014/0047903 A1 | 2/2014 | Sakai | |

FOREIGN PATENT DOCUMENTS

| | | | |
|---|---|---|---|
| CN | 104981477 A | 10/2015 | |
| CN | 106198943 A | 12/2016 | |
| DE | 0454952 A1 * | 11/1991 | ............ G01K 13/08 |
| EP | 0454952 A1 | 11/1991 | |
| EP | 0545728 A1 | 6/1993 | |
| EP | 1503211 A2 | 2/2005 | |
| WO | 2006125057 A1 | 11/2006 | |

OTHER PUBLICATIONS

China National Intellectual Property Administration, Office Action, 13 pages, dated Jun. 15, 2020 (English translation).

* cited by examiner

DEVICES AND METHODS FOR MEASURING VISCOELASTIC CHANGES OF A SAMPLE

CROSS-REFERENCE TO RELATED APPLICATIONS

This application is the U.S. national stage of PCT/EP2017/051660 filed Jan. 26, 2017, which is hereby incorporated by reference in its entirety.

FIELD OF THE INVENTION

The present invention relates to the field of viscoelastic analysis of a sample, in particular to hemorheology, for example to the viscoelastic analysis of blood and/or its elements, e.g. plasma and cells. The present invention is directed to devices, including detection devices and heating devices, and apparatuses for use in viscoelastic analysis, for example in coagulation testing of sample liquids, such as blood and/or its elements. The present invention is further directed to a method of performing such viscoelastic analysis, e.g. coagulation analysis, on a sample, such as a test liquid.

BACKGROUND OF THE INVENTION

Hemostasis is an essential physiological process that stops bleeding at the site of an injury by blot clotting (coagulation) while maintaining normal blood flow elsewhere in the circulation. Coagulation is triggered in case of injuries or inflammations by either extrinsic or intrinsic factors, e.g. tissue factor (TF) or Hagemann factor (F XII), respectively. Both cascades converge in a common mechanism resulting in the activation of thrombin—which cleaves soluble fibrinogen to generate insoluble fibrin. Fibrin fibers form a crosslinked fibrin mesh at the site of an injury.

Thrombocytes (platelets)—which undergo a number of physiological changes during the process of coagulation—are also implicated in the formation of the blood clot. Once the coagulation cascade has been triggered, thrombocytes aggregate between the fibrin mesh at the site of injury. Within limits, a lack of thrombocytes can be substituted by an increased amount of fibrin or vice versa. This is reflected by the observation that the thrombocyte counts as well as the fibrinogen concentration varies even within healthy patients.

Various tests of hemostasis have been developed to aid in identifying patients with hemostatic defects that could cause excessive bleeding. Such tests include thrombocyte counts or the determination of fibrin concentration. However, whereas such tests provide information as to the availability of thrombocytes or fibrin in sufficient amounts, they do not indicate whether thrombocytes, fibrin or other components of the coagulation cascade are biologically active and effective—i.e. effectively support coagulation under physiological conditions. Other common tests such as the prothrombin time (Quick-test) or the partial thromboplastin time (PTT) work on blood-plasma exclusively and therefore require an additional step for preparation of the plasma—which is time-consuming and therefore unfavorable especially under POC (point of care) conditions.

"Viscoelastic methods" have been developed in an attempt to overcome these problems. Said methods commonly determine the firmness of the forming blood clot (or other parameters dependent there on) in a continuous fashion: from the formation of the first fibrin fibers until the dissolution of the blood clot by fibrinolysis. Blood clot firmness is a functional parameter, which is important for hemostasis in vivo, as a blood clot must resist blood pressure and shear stress at the site of vascular injury. It results from multiple interlinked processes: coagulation activation, thrombin formation, fibrin formation and polymerization, platelet activation and fibrin-platelet interaction and can be compromised by fibrinolysis. Thus, viscoelastic methods allow for directly or indirectly assessing all of these inter-related mechanisms.

All viscoelastic methods rely on common setup: the blood sample (and forming blood clot) is placed in the space between a cylindrical pin and an axially symmetric cup. During coagulation (which is typically induced by the addition of one or more hemostasis activating factors), the forming fibrin scaffold creates a mechanical elastic linkage between the surfaces of the cup containing the blood sample and the pin immersed in the sample. Blood clot formation and—firmness is determined by assessing the ability of cup and pin to move relatively to each other. Thereby, various deficiencies of a patient's hemostatic status can be revealed and used for proper medical intervention.

The first viscoelastic method was called "thrombelastography" (Hartert H: Blutgerinnungsstudien mit der Thrombelastographie, einem neuen Untersuchungsverfahren. Klin Wochenschrift 26:577-583, 1948). The measurement apparatus (21) is depicted in FIG. 1: the sample (1) is placed in a cup (2) that is periodically rotated to the left and to the right by about 5°, respectively. A pin (3) is freely suspended by a torsion wire (4). When a blood clot is formed it starts to transfer the movement of the cup to the pin against the reverse momentum of the torsion wire. The movement of the pin as a measure for the blood clot firmness can be continuously recorded by optical detection means (5), such as light beam deflection, and plotted against time. For historical reasons, the firmness is thereby quantified in millimeters.

Modifications of the original thromboelastography technique (nowadays also called thromboelastometry) have been described by Hartert et al. (U.S. Pat. No. 3,714,815), Cavallari et al. (U.S. Pat. No. 4,193,293), Do et al. (U.S. Pat. No. 4,148,216), Cohen (U.S. Pat. No. 6,537,819), and by Calatzis et al. (U.S. Pat. No. 5,777,215).

In a measurement apparatus (121) according to U.S. Pat. No. 5,777,215, the sample (101) is also placed within a cylindrical cup (102) as shown in FIG. 2. However, the pin (103) is not plunged into the sample by a torsion wire, but by a metal shaft (106) that is fixed to a base plate by a ball bearing (107). The shaft (106) is periodically rotated by a sensitive spring (108) around its vertical axis. The movement of the pin as an inverse measure for the clot firmness can be again continuously recorded by optical detection means (105), such as light beam deflection, and plotted against time. Since the cup cannot be filled with the test liquid in measurement position, it is received by a cup holder that can be attached to the base plate of the measurement device.

The outcome of a typical measurement with setups according to FIG. 1 or 2 is illustrated in FIG. 3. One of the most important parameters is the clotting time (CT), i.e. the time between the time points of (i) (chemically induced) start of blot clotting and (ii) the formation of the first long fibrin fibers (indicated by the firmness signal exceeding a defined value). Another important parameter is the clot formation time (CFT), i.e. the time required for the clot firmness to increase from 4 to 20 mm. The CFT thus gives a measure for the velocity of the blood clot formation. The maximum clot firmness a (MCF), i.e. the maximum firmness achieved by a blood clot during measurement is also of great diagnostic importance. Further parameters obtainable from thromboelastographic measurement curves include the amplitude (A) at a certain time after CT (e.g., A10 is the amplitude 10 minutes after CT) and the lysis index (LI) in percent of amplitude reduction when compared to MCF at a certain time after CT (e.g., LI45 is the ratio between A45 and MCF in percent).

A general advantage of thromboelastometry as compared to common tests such as thrombocyte counts, fibrin concentration or PTT and the like is that the coagulation process and the change of mechanical properties of the sample are monitored as a whole. Thromboelastometry therefore does not only provide information about the availability of the components of the coagulation cascade (including thrombocytes, fibrinogen and other factors) in sufficient amounts but also indicates whether each component is biologically active and effective. In order to determine the amount and function of each component, such as thrombocytes, fibrinogen and other factors involved in coagulation, individually, a number of activators or inhibitors specifically targeting each component is commercially available. Accordingly, thromboelastometry allows to exactly determine at which point of a patient's coagulation system a problem is located.

To this end, state-of-the-art thrombelastometers which allow for conducting of several measurements in parallel. Thereby, detailed information on the current status of the coagulation-situation of a patient can be obtained and, based thereon, an appropriate therapy can be identified within a few minutes. Furthermore, the effects of therapeutic agents interfering with the coagulation cascade—whether intentionally or secondarily (e.g., as side effects)—can be tested in vitro prior to their application to the patient.

This is of particular importance in case of patients struck by massive blood loss as it often occurs in context with multiple traumata. The blood of such patients often is diluted due to infusions which are administered to replace the loss in volume. This leads to a decrease of the concentration of thrombocytes as well as coagulation factors such as fibrinogen.

Another important topic in this context is the determination of the fibrin networks contribution to the final stability of a growing blood clot. This can be achieved by adding a thrombocyte inhibitor, e.g. Cytochalisch D, to the sample before measurement. That way the activity of fibrin becomes directly accessible.

A major problem in thromboelastometric measurements results from decreasing signal-to-noise ratios in case of a reduced blood clot firmness of the evaluated sample. This typically occurs when patients struck by massive blood loss (e.g., in the case of multiple traumata) received infusions in order to replace the loss in blood volume. These infusions dilute the patient's blood, resulting in a decreased concentration of thrombocytes as well as coagulation factors such as fibrinogen. Inhibition of individual factors of the coagulation cascade for diagnostic reasons (as described above)—e.g. by adding a thrombocyte inhibitor such as Cytochalisch D in order to evaluate fibrinogen function and activity—or dilution with other agents can also lead to a reduced blood clot firmness and therefore a decreased signal-to-noise ratio and a loss of measurement accuracy.

This loss of accuracy is based on the fact that under the circumstances indicated above (e.g. dilution or addition of inhibitors of the coagulation cascade), thromboelastometric measurement is performed at the lower limit of sensitivity: the geometry of the standardized elements of the thromboelastometric measurement apparatus (the outer diameter of the pin typically being about 5.0 mm and the space between cup and pin being about 1.0 mm) and the amount of blood sample used per measurement were originally chosen to obtain the best signals when measuring conventionally activated and non-diluted blood clots of non-pathologic blood samples. Such tests result in values for the maximum clot firmness (MCF) between 50 and 70 mm, which is the most sensitively detected range of the method. When assessing pathologic, diluted or pre-treated blood samples, however, the maximum clot firmness can be considerably reduced. For instance, in blood samples treated with thrombocyte inhibitors, the blood clot is formed from fibrinogen only, resulting in MCF values between 15 and 25 mm for normal patients, while MCF values well below 10 mm are typically observed in the case of pathologic samples.

The general sensitivity level of viscoelastic tests (considering the actually well-established disposable geometry and the available ball-bearing technology for the axis that holds the pin) results in about 2 mm test-to-test variations (standard deviation). As a consequence, when measuring such samples with low amplitudes as mentioned above, the coefficient of variation easily exceeds 20%, rendering the definition of exact decision trigger values nearly impossible.

To achieve better accuracy, several approaches have been suggested in the past. However, despite those approaches (or due to their major drawbacks), the measurement setup used for viscoelastic testing of blood samples has not been changed much during the last 20 years. For example, U.S. Pat. No. 8,322,195 B2 discloses modifications of the geometry of pin and cup in order to improve signal quality for low-amplitude samples. This deviation from the widely used standard geometry, however, would require substantial regulatory efforts to become medically accepted. Another approach is described in U.S. Pat. No. 8,383,045 B2 and aims at improving the bearing technology for viscoelastic measurements, but it has not been introduced into the market so far.

Since a sufficient signal-to-noise ratio and measurement accuracy is crucial for a reliable diagnosis and appropriate treatment (where necessary) it would be an important achievement to increase the sensitivity of thromboelastometric tests. Apparatuses currently employed for thromboelastometric measurements typically rely on optical detections means that can be susceptible to soiling and/or vibrations, further decreasing measurement. In addition, detection and rotating means in the state-of-the-art apparatuses are typically attached to the pin, thereby increase the weight load thereon—which further reduces the accuracy of the obtained results, since such state-of-the-art apparatuses are quite susceptible to undesired interferences. There is thus a need in the art to provide means and methods that allow for a more accurate and reliable thromboelastometric measurement. Moreover, measurement apparatuses exhibiting an increased meantime between failure (MBTF) and requiring less service efforts and manufacturing costs at an enhanced usability are urgently needed.

SUMMARY OF THE INVENTION

In view of the above, it is the object of the present invention to overcome the drawbacks of current thromboelastic test devices and apparatuses as outlined above. Accordingly, it is an object of the present invention to provide an apparatus for measuring the coagulation characteristics of a test liquid, whereby the detection of the signal is i) less sensitive against dust or any other contaminations of the detection system, or ii) less sensitive against aging effects of the detection system components, and/or iii) cheaper to implement within a diagnostic device for medical use when compared to the currently available technologies. The improvements of the present invention take into account that any worsening of the signal quality due to higher weight load on the bearings (and correspondingly higher friction within the bearing) must be avoided or kept as small as possible to obtain medically valuable data with high accuracy.

The improvements of the present invention further consider that other disadvantages of prior art devices as resulting from their detection technologies—in particular, regarding complicated user handling or deficient robustness of the device—are also avoided. In particular, the improvements in the detection technology according to the present invention can be combined with substantial configuration changes of the measurement setup, in particular as it is not required anymore to place the bearing that is above the measurement cup. Moreover, the present invention also provides a temperature control unit having a very low volume. In summary, the present invention increases the degrees of freedom in constructing a measurement apparatus, and, thus, enables a measurement apparatus, which is easy to handle and to operate.

This is achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

As used herein, the term "viscoelastic" (in all its grammatical forms) is used interchangeably with the term "thromboelastic" (in all its grammatical forms). "Thromboelastic" or "viscoelastic" measurements or tests refer in particular to methods or apparatuses for testing the efficiency of blood coagulation.

The term "about" in relation to a numerical value x means $x \pm 10\%$.

Apparatus for Viscoelastic Analysis

The invention provides an improved apparatus for thromboelastic measurements and measurement methods exploiting these improvements. The inventive apparatus has been designed to overcome the drawbacks of state-of-the art thromboelastic tests. It comprises several beneficial features, which synergize to provide an improved overall measurement accuracy. Specifically, the inventive apparatus and methods are envisaged to have the following advantages of rendering the thromboelastic measurement: i) more accurate by reducing the weight load on the bearings (and thereby friction within the bearing) ii) easier to access and handle and more robust due to the unique design of the apparatus, iii) less sensitive against the deposition of dust or any other contaminations/soiling of the detection system, and/or iv) less sensitive against aging effects of the detection system components, and/or v) cheaper to implement within a diagnostic device for medical use when compared to the currently available technologies. Due to its novel and improved design resulting in an increased measurement accuracy, the inventive apparatus allows for evaluating "standard" blood samples, but also diluted (e.g. due to prior infusion) or pre-treated (e.g. with a thrombocyte inhibitor) blood samples and thereby opens up new potentials in blood coagulation measurement.

In a first aspect the present invention provides an apparatus for measuring the coagulation characteristics of a sample comprising:

a cup suitable for receiving the sample;

a cup receiving element providing (detachable) fixing for the cup in measurement position;

a pin suitable to be dipped into said sample in said cup, wherein the pin is rotational symmetric, the rotational symmetry axis of the pin forms a vertical axis, and the pin is attached to supporting means;

rotating means comprising a shaft, which extends along the vertical axis, which is rotatable around the vertical axis, and which is attached to the cup receiving element or to supporting means for the pin, such that a rotation of the shaft causes a rotation of the cup receiving element or of the supporting means for the pin, and/or vice versa; and detection means capable of detecting a rotation around said vertical axis and/or variations in a rotation around said vertical axis;

wherein the rotating means are provided below the cup, pin and cup receiving element.

The sample to be evaluated by use of the apparatus according to the present invention is preferably liquid. Accordingly, it is also referred to herein as "liquid sample", "sample liquid" or "test liquid". More preferably the sample liquid comprises or consists of a biofluid (also referred to as "body fluid"), i.e. a fluid originating from an organism, in particular a fluid originating from a human or an animal. Even more preferably the sample liquid comprises or consists of blood, preferably whole blood, or one or more of its elements/components, e.g. plasma and/or cells. Particularly preferably the sample comprises or consists of a human blood sample and comprises (whole) blood and/or blood plasma.

Optionally, the sample may further comprise one or more of the following additional components, e.g., (a) one or more activators of coagulation, including without limitation,
   (i) extrinsic activators such as Tissue factor (TF, also referred to as platelet tissue factor, factor III, thromboplastin, or CD142);
   (ii) intrinsic activators (e.g. celite, ellagic acid, sulfatit, kaolin, silica, or RNA, or mixtures thereof);
(b) one or more inhibitors of coagulation, including without limitation,
   (i) fibrinolysis inhibitors (e.g. aprotinin, tranexamic acid, eaca, thrombin-activated fibrinolysis inhibitor, plasminogen activation inhibitor ½, α2-antiplasmin, or α2-macroglobulin or mixtures thereof);
   (ii) platelet inhibitors (e.g. cytoskeleton inhibitors such as Cytochalasin D or a GPIIb/IIIa antagonist, preferably Abciximab, or mixtures thereof);
   (iii) heparin inhibitors (e.g. heparinase, protamine or protamine-related peptides and their derivatives, or other cationic polymers, for example hexadimethrine bromide (polybrene) or mixtures thereof);
(c) coagulation components; and/or
(d) other components, including calcium salts (e.g. calcium chloride and/or calcium lactate and/or calcium gluconate), stabilizers (e.g. albumin or gelatin), or phospholipids (e.g. phosphatidylserine, phosphatidylethanolamine, phosphatidylethanolcholine or mixtures thereof).

Depending on the diagnostic aim, the above described additional components can be used either alone or in combination: For example, a measurement with a combination of extrinsic activator and platelet inhibitor (e.g., Cytochalasin D) in the sample can be applied to determine the activity of fibrinogen without platelet contribution in the sample. Advantageously, the apparatus according to the present invention is capable of reliably determining the coagulation characteristics of a variety of different samples, in particular (pathogenic) blood samples or pre-treated or diluted blood sample that exhibit an impaired coagulation capacity as compared to healthy, untreated and/or undiluted controls.

As used herein, the term "measurement accuracy" or "accuracy" is used interchangeably with the terms "measurement precision" or "precision". "Accuracy" or "precision" is in particular discussed in terms of the standard deviation (SD) and percent coefficient of variation (% CV). Standard deviation is a measure of the variability (scatter of a method). Its normal distribution gives a bell shaped curve. The % CV describes the SD as a percent of the average value. The viscoelastic test apparatus of the invention preferably provides results with a SD of less than 20%, more preferably of less than 15%, even more preferably of less than 10%, and most preferably of less than 5%.

As used herein, the term "cup" (also referred to as "measurement cup", "cuvette" or "test cell") refers to a cup that receives the sample to be measured, in particular in the viscoelastic test (e.g., blood or blood components). Accordingly, the term "cup" refers in particular to a measurement cup, such as a cuvette or a test cell, in particular to be used in coagulation testing, such as in viscoelastic measurement. Preferably, the cup has a cylindrical or tapered shape. The cup, in particular the cylindrical or tapered cup, preferably comprises (i) an upper open end that allows insertion of a pin prior to a viscoelastic measurement; and (ii) a closed lower end designed to receive the sample. Preferably, the upper open end of the cup and the closed lower end of the cup have a circular shape. It is also preferred that the upper open end of the cup has a diameter from 5 to 10 mm. Moreover, it is also preferred that the diameter of the (circular) upper open end of the cup is not smaller than the diameter of the (circular) closed lower end. Preferably, the cup has a cylindrical shape, whereby the diameter of the (circular) upper open end of the cup and the diameter of the (circular) closed lower end of the cup are about the same size. It is also preferred that the cup has a tapered shape, whereby the diameter of the (circular) upper open end of the cup is larger than the diameter of the (circular) closed lower end of the cup. Preferably, the closed lower end of the cup has no sharp edge along the border to the (cylindrical) sidewall of the cup. Preferably, the closed lower end of the cup has a radius of at least 0.25 mm, more preferably of about 1 mm or more.

Preferably, the cup is a plastic cup, more preferably the cup is a disposable plastic cup. Preferably, the cup is made of a plastic material that can be injection-molded. Preferably, the cup is made of an injection-molding compatible polymer material. Preferred examples thereof include polystyrene (PS), polymethyl methacrylate (PMMA), methyl methacrylate acrylonitrile butadiene styrene (MABS), polyamide (PA), polysulfone, polycarbonate (PC), polyethylene (PE), polypropylene (PP), or the like or any other suitable material which does not affect coagulation activation before or after a possible sample treatment. It is also preferred that the cup is not made of a material containing glass or metal, e.g. sheet metal and/or aluminum foil, more preferably the cup does not contain any glass or metal, e.g. sheet metal and/or aluminum foil.

The cup receiving element is configured to receive and support said cup. The cup receiving element will therefore have a shape, which corresponds to the shape of the cup, for example typically a cylindrical shape or a tapered shape. It will be readily acknowledged that in order to be capable of receiving and supporting the cup during viscoelastic measurement, the cup receiving element should have dimensions that exceed those of the cup.

The cup receiving element provides fixing for the cup in the measurement position. For example, the cup receiving element may have a shape, which corresponds to the outer shape of the cup, such that no further fixation means are required for fixing the cup in the measurement position. Alternatively, fixation means known in the art may be used. Preferably, the fixation of the cup in the cup receiving element is detachable, such that disposable cups can be used, which are typically discarded, e.g. after single use/measurement.

Preferably, the cup receiving element comprises an open top portion for receiving the cup prior to a viscoelastic measurement, and a closed bottom portion. Preferably, the top portion and the bottom portion of the cup receiving element have a circular shape. It is also preferred that the diameter of the (circular) top portion of the cup receiving element is not smaller than the diameter of the (circular) bottom portion. Preferably, the cup receiving element has a cylindrical shape, whereby the diameter of the (circular) top portion of the cup receiving element and the diameter of the (circular) bottom portion of the cup receiving element are about the same size. It is also preferred that the cup receiving element has a tapered shape, whereby the diameter of the (circular) top portion of the cup receiving element is larger than the diameter of the (circular) bottom portion of the cup receiving element. The bottom portion of the cup receiving element may have a radius of at least 0.30 mm, more preferably of about 1 mm or more, wherein said radius exceeds the radius of the bottom portion of the cup to be supported by said cup receiving element.

Preferably, the cup receiving element comprises temperature control means to control the temperature of the cup and/or of the sample. For example, the cup receiving element may be heated directly, e.g. by electronic heating elements such as thermal resistors or Peltier elements. The cup receiving element may also be heated indirectly, e.g. by radiation from a remote heating source. To control the temperature at a certain level a thermal sensor may be used to measure the temperature to which the heat source may then be adjusted. Such a thermal sensor may be directly attached to the cup receiving element (e.g., a thermocouple or a thermal sensitive resonance circuit), or be a remote thermal sensor (e.g., a pyroelectric sensor).

Preferably, the cup receiving element comprises a cup receiver for fixing the cup and fixation means for attaching the cup receiver to the shaft or to other portions of the apparatus, in particular to immovable portions of the apparatus. The cup receiver provides a fixation of the cup in a certain position, i.e. due to the cup receiver the cup cannot be moved or rotated in its position. For example, the cup receiver may be formed as a hollow cylinder with an inner diameter that is only slightly (e.g., 0.01 to 0.1 mm) greater than the outer diameter of the cup and the cup receiver may "receive" the cup by pushing the cup's lower end into the opening of the hollow cylinder. Alternatively, the cup receiver may also be formed by a squeezing mechanism, for example by providing a spring force to the outer surface of the cup. In particular, the cup receiver is fixed/attached to the shaft or to other portions of the apparatus, in particular to immovable portions of the apparatus, by fixation means. The fixation means may be any fixation means known in the art. For example, the fixation means may be a thread to screw the cup receiver on/to the shaft or to other portions of the apparatus, in particular to immovable portions of the apparatus, or the fixation means may be, for example, a fit/fitting to press/attach the cup receiver on/to the shaft or to other portions of the apparatus, in particular to immovable portions of the apparatus.

The term "pin" as used herein (also referred to as "measurement pin" or "probe") refers to an element for performing a viscoelastic test (cf. FIGS. 1, 2, 4, 5, 11). Typically, for performing a viscoelastic test the sample to be tested, e.g. a (whole) blood sample, is provided in the measurement cup as described above. For the viscoelastic test, typically a pin is dipped into the cup, thereby typically contacting the sample, e.g. a (whole) blood sample. Preferably, the pin is immerged into the sample, e.g. a (whole) blood sample. Preferably, the pin used to perform the viscoelastic measurement has a radius of similar size, preferably of about the same size, more preferably of the same size, along its outer edge between lower end and cylindrical sidewall as the cup has along its inner edge between lower end and cylindrical sidewall (cf. FIGS. 4, 5, 11).

The pin preferably comprises a pin neck (i.e. an elongated portion) connected to a pin head (i.e. a bulge portion suitable to be immersed into the cup, the pin head typically having a larger diameter than the pin neck). It will be understood that the outer diameter of the pin head forming the sample contacting portion has to be smaller than the inner diameter of the cup comprising the sample such that the pin head can be inserted into the cup. The pin is preferably made of a polymer material, for example of an acrylic or styrene polymer material, such as PMMA, MABS, ABS, PS, or any mixed co-polymer thereof or any other material which does not affect coagulation activation before or after a possible sample treatment.

As described above, during measurement, the pin is typically dipped/immersed into the sample provided in the cup. Thereby, the pin contacts at least partially (i.e., at least the tip of the pin or the pin head) the sample. The detection of the characteristic parameters of the sample, e.g. the blood forming a clot, is typically based on the (mechanical) coupling of cup and pin which is established by the formation of, e.g., a clot (cf. FIG. 3). Typically, in the apparatus according to the present invention, either the pin is moved, preferably rotated, whereas the cup is stationary at the beginning or stays stationary throughout the measurement—or the cup is moved, preferably rotated, whereas the pin is stationary at the beginning or stays stationary throughout the measurement. After the formation of, for example, a clot between cup (cuvette) and pin, the clot itself is stretched by the movement of the pin relative to the cup or of the cup relative to the pin. For example, the cup may rotate and the pin is stationary at the beginning, but able to rotate as well. Upon clot formation in this case the pin may typically start to rotate, which can be measured. In a preferred example, the pin rotates and the cup stays stationary throughout the measurement, whereby upon clot formation the initial unrestricted rotation of the pin starts to encounter increasing impedance as the clot strength increases, which is typically measured, e.g. by detection by an optical system.

To enable a rotation of the pin inside the cup or of the cup around the pin, the pin (and preferably also the cup) is rotational symmetric. This means that in particular a (horizontal) cross section of the pin has a rotational symmetric shape. Preferably, all horizontal cross sections of the pin have a rotational symmetric shape. More preferably, the pin has a cylindrical or a tapered shape with an essentially circular cross section. The rotational symmetry axis of the pin (i.e. the axis which is essentially perpendicular to the rotational symmetric, preferably essentially circular, (horizontal) cross section) forms a vertical axis.

As used herein, i.e. throughout the present application, the terms "rotation" and "rotating" refer to the circular movement/moving around an axis/center, in particular around the vertical axis. The term "rotatable" refers to the capability to do so. Preferably, an rotatable element is during normal use of the apparatus (i.e. without application of violent force) not moveable in any other direction and/or way, in particular with the exception of very small movements, which do not normally impair measurement accuracy. The terms "rotation", "rotatable" and "rotating" refer to "full" rotations (around the complete 360°) and to partial rotations (not around the complete 360°, but only to a part (certain angle) thereof). A rotation may occur in one direction only or in both directions. The terms "rotation", "rotatable" and "rotating" are thus understood to include "oscillation" and "oscillating", i.e. alternately (partially) rotating back and forth around an axis (in particular vertical axis), e.g. between two fixed positions. "Oscillation" and "oscillating" therefore refers in particular to a (small) angular back and forth rotation (e.g., +/−2.5°) around an axis. A "rotatable" element will therefore be understood as being capable of fully or partially rotating, and fully or partially oscillating, as required for most viscoelastic tests. In particular, a complete (full) rotation of 3600 around an (vertical) axis is not even required for most viscoelastic tests—typically a partial rotation of, for example, +/−2.5° around a (vertical) axis (i.e., in both directions) is sufficient for viscoelastic testing. A partial rotation is also referred to herein as small angular movement or as (partial) circular motion. Preferably, the angular range of the partial rotation or oscillation is (covers) no more than 60°, preferably of no more than 30°, more preferably of no more than 20°, even more preferably of no more than 10°, still more preferably of no more than 5° and most preferably of about 2.5°.

The pin, preferably the pin neck, is attached to supporting means. Such an attachment may preferably be detachable, such that the pin can be removed, for example for cleaning of the pin. The attachment may be fixed or movable. Preferably, the attachment of the pin to the supporting means is fixed, i.e. if the supporting means are immobile, also the pin is immobile; and/or if the supporting means move/rotate the pin performs essentially the same rotation/movement.

As used herein "supporting means" refers to any means, which can be used for support, for example of the pin. Typically the supporting means for the pin provide the attachment of the pin to the "body" of the apparatus according to the present invention. Accordingly, the design/shape of the supporting means may depend on the overall design of the apparatus.

Preferably, the supporting means of the pin are immobile/immovable, such that preferably also the pin attached to the supporting means is immobile, such that the pin is fixed in an immobile manner. Embodiments of the present invention with such an immobile/immovable pin are also referred to herein as "rotatable cup" embodiments, because in those embodiments typically the cup/cup receiving element will be (partially) rotatable. As used herein, "fixed in an immobile manner" means that the element, e.g., the pin or the cup/cup receiving element, is fixed in a position that substantially neither allows the element to move in a rotational movement around the vertical axis, nor in any other direction. In this context, "substantially" means that minimal movements of the element may not always be prevented, and that such minimal movements may be tolerated in case they do not significantly reduce the measurement accuracy of the apparatus. Specifically, the apparatus should be able to evaluate pre-treated, pathologic and/or diluted blood samples with an adequate measurement accuracy (i.e. preferably with an SD of less than 20%, more preferably of less than 15%, even more preferably of less than 10%, and most preferably of less than 5%). For example, for immovable/immobile/stationary attachment of the pin, any immovable/immobile/stationary part of the apparatus may be used, such as (a part of) the housing of the apparatus, e.g. a cover. Thus, the supporting means for the pin are preferably configured as a cover. For example, the pin can be attached (fixed) to an upper plate of the apparatus in an immobile manner, e.g. via its pin neck.

Alternatively, the cup and/or cup receiving element can be attached to any immovable/immobile/stationary part of the apparatus, such as (a part of) the housing of the apparatus, e.g. an upper plate. Accordingly, the cup receiving element may be attached (fixed) in an immobile manner, e.g. by means of an upper plate comprising a suitable opening/aperture for receiving the cup/cup receiving element, e.g. via its rim or the like.

It is also preferred (in particular in the case of an immobile cup/cup receiving element as described above, but also in general) that the supporting means for the pin are (partially) rotatable, such that preferably also the pin is (partially) rotatable. Embodiments of the present invention with such an (partially) rotatable pin are also referred to herein as "rotatable pin" embodiments. For such "rotatable pin" embodiments the supporting means for the pin is preferably a (curved) rod or tube or a frame. Preferably, the movable supporting means for the pin, in particular the frame, are made of a material comprising metal, more preferably they are made of metal. Preferably, the movable supporting means for the pin are a frame. As used herein the term "frame" typically refers to a rigid structure formed of relatively slender pieces (or a single piece) so as to surround an area. In other words, a "frame" is in particular an arrangement of connected/joined relatively slender elements, such as rods or tubes, or a single relatively slender element formed accordingly (such as a single curved rod or tube), which forms a closed outline of an area. Preferably the frame has an essentially circular, ellipsoid, triangular, quadrangular, pentagonal, hexagonal, heptagonal, octagonal or any polygonal, or even irregularly shape. Thereby, "essentially triangular, quadrangular, pentagonal, hexagonal, heptagonal, octagonal or any polygonal" in particular also includes embodiments with rounded corners, such as rounded triangular, rounded quadrangular, rounded pentagonal, rounded hexagonal, rounded heptagonal, rounded octagonal shapes. Preferably, the movable/rotatable supporting means for the pin have (at least) a bilateral symmetrical shape. Thereby, a steady and balanced movement/rotation of the pin is ensured. More preferably, the frame has an essentially rectangular shape, in particular a rounded rectangular shape (i.e. with rounded corners).

The apparatus according to the present invention further comprises rotating means comprising a shaft, which shaft
- extends along the vertical axis,
- is rotatable around the vertical axis, and
- is attached to the cup receiving element or to supporting means for the pin, such that a rotation of the shaft causes a rotation of the cup receiving element or of the supporting means for the pin, and/or vice versa.

Accordingly, the rotating means provide a rotation to the cup receiving element (and, thus, to the cup) or to the supporting means for the pin (and, thus, to the pin). To this end, the rotating means comprise a shaft, which is directly or indirectly attached to the cup receiving element or to supporting means for the pin.

The shaft extends along the vertical axis and is rotatable around the vertical axis. Thus, the shaft is also referred to as a "rotatable shaft" herein. The shaft is typically disposed below the cup/cup receiving element and the pin. The shaft is thus connected to the supporting means for the pin or to the cup/cup receiving element (typically a cup receiving element which supports a (disposable) cup that can be easily exchanged or refilled for each measurement), thus rendering either of both elements rotatable whereas the other element is typically fixed.

In the preferred "rotatable cup" embodiments of the invention, the shaft is connected to (attached to) (the bottom portion of) the cup receiving element so as to transfer rotation/oscillation to/of said cup receiving element around the vertical axis. In other words, the shaft is preferably attached to the cup receiving element, in particular to the bottom of the cup receiving element, such that a rotation of the shaft causes a rotation of the cup receiving element and/or vice versa. The shaft is typically attached to (the bottom portion of) said cup receiving element via its upper end. In those "rotatable cup" embodiments, the pin is preferably fixed in an immobile manner as described above, e.g. via its pin neck, optionally to an upper plate or to a cover as described above. A preferred "rotating cup" embodiment is shown in FIG. 4 and described in more detail below.

In the preferred "rotatable pin" embodiments of the invention, the shaft is connected to the supporting means for the pin, so as to transfer rotation/oscillation to/of said supporting means for the pin (and, thus, to the pin) around the vertical axis. In other words, the shaft is preferably attached to supporting means for the pin, such that a rotation of the shaft causes a rotation of the supporting means for the pin (and, thus, of the pin), and/or vice versa. In those "rotatable pin" embodiments, the cup/cup receiving element is preferably fixed in an immobile manner, such that the cup attached to the cup receiving element is fixed in an immobile manner. optionally to an upper plate. For example, for immovable/immobile/stationary attachment of the cup receiving element, any immovable/immobile/stationary part of the apparatus may be used, such as an upper plate or housing (part) of the apparatus. A preferred "rotating pin" embodiment is shown in FIG. 5 and described in more detail below.

Rotation of the shaft is preferably achieved by an elastic coupling element. Thus, the rotating means preferably comprise an elastic coupling element, which provides a rotation to the shaft. In this context to "provide a rotation to the shaft" means in particular to "cause a rotation of the shaft". The shaft then transfers the rotation generated by the elastic coupling element (a) to the supporting means for the pin (and, thus, to the pin, preferably via the pin neck), or (b) to the cup receiving element (and, thus, to the cup); thereby allowing the cup and/or the pin to rotate (or oscillate) relatively to each other.

The rotating means provide a rotation to the cup receiving element (and, thus, to the cup) or to the supporting means for the pin (and, thus, to the pin), so as to allow rotation of the cup receiving element (and, thus, of the cup) or of the supporting means for the pin (and, thus, of the pin) around the vertical axis, in particular in an angular range of at least 1°, more preferably at least 2°, and more preferably at least 4°.

Preferred examples of an elastic coupling element (which provides a rotation to the shaft) include a spring wire, a piezo-electric bending element, or a field-based forcing element using an electric force (e.g., applied by inducing a charge difference between a first capacitor electrode attached to the shaft and a second capacitor electrode attached to the base plate) or using a magnetic force (e.g., applied by generating a first magnetic field within the shaft or within a magnetic element attached to the shaft and a second magnetic field within a magnetic element attached to the base support member of the apparatus, such as a base plate).

Preferably, the elastic coupling element is a spring wire. If a spring wire is used for generating a torque acting (rotation) onto the shaft, one end of the spring wire may be fixed to the shaft. Preferably, the spring wire is positioned (in a plane) below a (ball bearing) and essentially parallel thereto.

Preferably, the elastic coupling element is a piezo-electric bending element. If a piezo-electric bending element is present for generating a torque acting onto the shaft, one end of the bending element may be fixed to the shaft and the other end may be fixed to the base support member of the apparatus, such as a base plate. The rotation may then be generated by applying selective voltage changes to the piezo-electric bending element, which results in corresponding bending movements.

Preferably, the elastic coupling element is a field-based forcing element using an electric force. If an electric force is used to generate a torque acting (rotation) onto the shaft, one small, isolated metal electrode may be attached to the shaft with its plane extending perpendicular from the shaft, and a second and third metal electrode may be attached to the base support member of the apparatus, such as a base plate, for example essentially parallel to (a part of) a detection means, such as a (first) capacitor plate. The first electrode may receive a defined charge of electrons, e.g., by electrically connecting to a charge reservoir before each measurement starts. If the second electrode also receives a charge by being connected to an electron reservoir, a repelling force between both electrodes occurs. Since the repelling force is the lower, the longer the distance between both electrodes, the rotating movement of the shaft will stop at a certain point as defined by the charge size on both plates. If the charge is selected as such the first electrode is not yet touching the third electrode when stopping, a counter movement can be induced by clearing the charges on the second electrode and filling the third electrode with a similar amount of charges as the second electrode. By alternating clearing and filling of charges onto the second and third electrodes, the required movement for thromboelastic measurements can be generated.

Preferably, the elastic coupling element is a field-based forcing element using a magnetic force. If a magnetic force is used to generate a torque acting (rotation) onto the shaft, a (small) magnet may be attached to the shaft having a distance d to the axis and with its permanent magnetic field (or at least a component of its permanent magnetic field) tangentially oriented to the distance d. By applying an external magnetic field with controllable intensity and/or direction (e.g., a magnetic field induced by an electric current in a solenoid coil) to the magnetic field of the magnet attached to the shaft, a rotation in can be applied in both directions as required for a thromboelstometric measurement.

To avoid friction problems caused by the rotation of the shaft relative to adjacent fixed parts of the apparatus (for example in the base support member of the apparatus, if the rotatable shaft extends through the base support member), the rotating means preferably also contain a bearing, preferably with low friction torque. In general, a bearing is an element that constrains relative motion to only the desired motion, and reduces friction between moving parts. Preferably, the bearing is selected from a roll bearing, in particular a ball bearing; a magnetic bearing; and an air-lubricated bearing.

A roll bearing (also referred to as "rolling-element bearing" or "rolling bearing") is a bearing which carries a load by placing rolling elements (such as balls or rollers) between two bearing rings called races. The relative motion of the races causes the rolling elements to roll with very little rolling resistance. Preferred roll bearings include ball bearings and roller bearings.

A ball-bearing has inner and outer races between which balls roll. In particular, a ball bearing uses balls to maintain the separation between the bearing races. The purpose of a ball bearing is to reduce rotational friction and support radial and axial loads. It achieves this by using at least two races to contain the balls and transmit the loads through the balls. Preferably, one race is stationary and the other is attached to the rotating assembly (e.g., a hub or shaft). As one of the bearing races rotates it causes the balls to rotate as well. Because the balls are rolling they have a much lower coefficient of friction than if two flat surfaces were sliding against each other. Particularly suitable is radial groove ball bearing of small diameter, for example 3 to 5 mm. Other ball bearings like thrust ball bearings, or roller bearings can also be employed.

Roller bearings typically have higher load capacity than ball bearings, but a lower capacity and higher friction under loads perpendicular to the primary supported direction. Preferred examples of a roller bearing include a cylindrical roller bearing, a spherical roller bearing, a gear bearing, a tapered roller bearing, a needle roller bearing, and a CARB toroidal roller bearing.

Cylindrical roller bearings use cylinders of slightly greater length than diameter.

Spherical roller bearings have an outer ring with an internal spherical shape. The rollers are thicker in the middle and thinner at the ends. Spherical roller bearings can thus accommodate both static and dynamic misalignment.

A gear bearing is a roller bearing combining to epicyclical gear, wherein each element of it is represented by concentric alternation of rollers and gearwheels with equality of roller(s) diameter(s) to gearwheel(s) pitch diameter(s). The widths of conjugated rollers and gearwheels in pairs are the same. The engagement is herringbone or with the skew end faces to realize efficient rolling axial contact.

Tapered roller bearings use conical rollers that run on conical races. Most roller bearings only take radial or axial loads, but tapered roller bearings support both radial and axial loads, and generally can carry higher loads than ball bearings due to greater contact area.

Needle roller bearings use very long and thin cylinders. Often the ends of the rollers taper to points, and these are used to keep the rollers captive, or they may be hemispherical and not captive but held by the shaft itself or a similar arrangement.

CARB bearings are toroidal roller bearings and similar to spherical roller bearings, but can accommodate both angular misalignment and also axial displacement. Compared to a spherical roller bearing, their radius of curvature is longer than a spherical radius would be, making them an intermediate form between spherical and cylindrical rollers.

A magnetic bearing is a bearing that supports a load using magnetic levitation. Magnetic bearings support moving parts without physical contact. For instance, they are able to levitate a rotating shaft and permit relative motion with very low friction and no mechanical wear. Magnetic bearings support the highest speeds of all kinds of bearing and have no maximum relative speed.

An air-lubricated bearing (also referred to as "air bearing", "aerostatical bearing" or "aerodynamical bearing") is a bearing that uses a thin film of pressurized air to provide an exceedingly low friction load-bearing interface between surfaces. The two surfaces do not touch. As they are contact-free, air bearings avoid the traditional bearing-related problems of friction, wear, particulates, and lubricant handling, and offer distinct advantages in precision positioning, such as lacking backlash and static friction, as well as in high-speed applications.

Roll bearings, in particular ball bearings are more preferred. Most preferably, the rotating means comprise a ball bearing. Particularly suitable is a deep groove ball bearing of small diameter, for example 3 mm. The use of a ball bearing has the advantage of reducing susceptibility to shocks and vibrations. The bearing preferably functions as frictionless as possible.

The rotating means can in principle be configured also in any other ways, as long as they are capable of generating a rotation. Said rotation is then transferred via the rotatable shaft to either the cup receiving element and, thus, to the cup ("rotating cup" embodiments); or to the supporting means for the pin and, thus, to the pin ("rotating pin" embodiments).

In apparatuses for measuring blood coagulation characteristics known in the art, the rotating means (e.g. the elastic coupling element and/or the (ball) bearing) are typically disposed in the upper part of the apparatus, in particular above the pin (cf. U.S. Pat. No. 5,777,215 A), thereby placing an additional weight load on the pin, which renders measurements inaccurate. Viscoelastic measurements rely on the detection of even small changes in the angular movement of the pin or cup. Therefore, any additional weight load placed on the pin severely impairs measurement accuracy. In order to overcome this problem, the present inventors developed an apparatus for measuring coagulation characteristics, wherein the rotating means are provided below the cup, the pin and the cup receiving element. For example, the rotating means can be disposed above, below or within a base support member. Preferably, the elastic coupling element is disposed above or below the base support member of the apparatus. Preferably, the bearing, in particular the ball bearing, is disposed in the base support member, such as a base plate, of the apparatus. It is also preferred that the rotatable shaft extends through the base support member, in particular, the rotatable shaft extends through the base support member and through the bearing disposed therein. In this way, the (fixed) base support member bears the rotatable shaft without (or nearly without) any friction problems caused by the rotation of the shaft.

In "rotatable pin" embodiments it is preferred that the cup receiving element is attached (fixed) in an immobile manner in an upper plate of the apparatus, which comprises a suitable opening/aperture for receiving the cup/cup receiving element, e.g. via its rim or the like, as described above. In such embodiments the pin is typically attached to the supporting means for the pin (e.g., the frame as described above) above the upper plate of the apparatus, whereas the shaft—and other (optional) components of the rotating means—is/are disposed below the cup, cup receiving element and pin and, thus, below the upper plate. Since in such "rotatable pin" embodiments the supporting means for the pin connect the pin (above the upper plate) with the shaft/rotating means (below the upper plate), the supporting means in such embodiments typically extend through the upper plate. To this end, it is preferred that the upper plate comprises suitable openings, which enable a (partial) rotation of the supporting means extending through the upper plate. Such a suitable opening may, for example have a round shape (like a segment of a circle) to enable partial rotation. For bilaterally symmetrically frames two such openings may be provided in the upper plate. In this context it is particularly preferred that angular range of the partial rotation or oscillation is (covers) no more than 60°, preferably of no more than 30°, more preferably of no more than 20°, even more preferably of no more than 10°, still more preferably of no more than 5° and most preferably of about 2.5°, such that the corresponding openings in the upper plate can be relatively small to keep the upper plate as stable as possible and to receive the cup/cup receiving element.

The apparatus according to the present invention further comprises detection means capable of detecting a rotation around the vertical axis and/or variations in a rotation around the vertical axis. In the context of coagulation characteristics it is most important that the detection means can used to determine variations in the rotation around the vertical axis. In particular, the formation of a blood clot counteracts/"impairs" the rotation as provided by the rotation means. For example, the rotation may be delayed and/or an increased "force" may be required to maintain rotation.

Preferably, the detection means are selected from optical, electrical, or magnetic detection means. Preferably, the detection means are electrical detection means; more preferably, the electrical detection means are capacitive detection means, for example as described herein. Electrical detection means can be provided, for example, by implementing a capacitive sensor that detects changes of the electrical field strength as induced by electrical conductor plates attached to the vertical axis and moved by axis rotation. Preferably, the detection means are magnetic detection means. Magnetic detection means can be provided, for example, by implementing a magnetic sensor that detects changes of the magnetic field strength as induced by magnets attached to the vertical axis and moved by axis rotation.

Preferably, the detection means are optical detection means, preferably comprising a light emitter (such a light source, for example for visible light) and a light sensor (e.g., a photo sensor which is able to detect the emitted light, i.e. which is typically sensitive for the corresponding wavelength range). Preferably, the optical detection system further comprises a mirror, in particular which may be mounted to the pin (e.g., to the pin neck; or to an element connected to the pin, e.g., a "prolongation" of the pin/pin neck). The mirror can be used for reflecting a light beam from a light source towards a photo detector such that the rotational position of the shaft of the pin is detectable. Such optical detection means are for example described in U.S. Pat. No. 5,777,215 A.

The detection means are preferably disposed below the pin, the cup and the cup receiving element, thereby avoiding any additional weight load on the pin. The detection means are preferably disposed within or below the base support member, e.g. the base plate, of the apparatus. The detection means are preferably connected to the, in particular to its lower end.

Preferably, the detection means comprise one or more capacitor elements. In other words, it is preferred that the detection means are capacitive detection means. Capacitive detection means are based on capacitive coupling. Capacitive coupling is the transfer of energy within an electrical network or between distant networks by means of displacement current between circuit(s) nodes, induced by the electric field. Preferably, such an capacitor element comprises an electrically non-conductive support, which preferably extends essentially perpendicularly to the vertical axis of the apparatus and at least one electrically conductive and rotatable layer disposed on the support, which preferably rotates with the same angular amplitude as the shaft. Preferred examples of the electrically non-conductive support and of the at least one electrically conductive and rotatable layer disposed on the support are described below in the context of the capacitive detection means according to the present invention. Furthermore, it is also preferred that the detection means further comprises an electrical circuit capable of detecting a rotation of at least +/−2° with an accuracy of at least 0.2° on a time frame of at most 5 seconds as described below in the context of the capacitive detection means according to the present invention.

Capacitive Detection Means

In a second aspect the present invention provides a capacitive detection means for detecting variations in a rotation around a vertical axis caused by blood coagulation. Usually, apparatuses for viscoelastic measurement employ optical detection means, i.e. typically a mirror mounted to the pin for reflecting a light beam from a light source towards a photo detector such that the rotational position of the shaft of the pin is detectable. While such optical detection means are combinable with the apparatus according to the present invention as described above, they may also exhibit certain disadvantages. In particular, such optical detection means are more prone to measurement errors due to deposition of dust or other contaminants on the mirror. Such disadvantages are overcome by the capacitive detection means according to the present invention.

Accordingly, the present invention provides a capacitive detection means for detecting variations in a rotation around a vertical axis caused by blood coagulation comprising
  a rotatable capacitor element capable of rotating around the vertical axis;
  at least one fixed capacitor element; and
  an electrical circuit, which is preferably connected to the at least one fixed capacitor element;
wherein (i) each of the capacitor elements comprises at least one electrically conductive element, which does not have a circular shape with the vertical axis as center, and (ii) the rotatable capacitor element and the at least one fixed capacitor element are arranged such that the electrically conductive element(s) of the rotatable capacitor element face the electrically conductive element(s) of the at least one fixed capacitor element.

In general, the electrically conductive elements of the rotatable capacitor element and of the fixed capacitor element, which face each other, function in a similar manner as the two conductive plates of a parallel-plate capacitor. To detect a rotation of the rotatable capacitor element relative to the fixed capacitor element, the electrically conductive elements of the capacitor elements can have any shape, except for a circular shape with the vertical axis (i.e. the rotation axis) as center. The reason is that a rotation (or a variation in the rotation) can be detected by a variation in the capacitance (or by charge fluctuation). Due to their shape (which is not a circular shape with the rotation axis as center), the distance between the electrically conductive elements of the rotatable capacitor element and of the fixed capacitor element changes during rotation, which results in a variation in the capacitance.

However, it is also conceivable that the at least one electrical conductive element on the first capacitor element merely provides an "electric environment" for at least two (capacitor) electrodes (electrical conductive elements), which are located on the second (i.e. on the other) capacitor element. Again, rotation of one electrically conductive element relative to the other induces capacitance differences/charge fluctuations, although in this case they are induced by a change in the electrical environment due to the rotation. In such a configuration it is preferred that grounded electrodes are located between the at least two (capacitor) electrodes (electrical conductive elements), which are located on the second (i.e. on the same) capacitor element, in order to minimize direct capacitive charge variations among those electrodes located on the same capacitor element.

In general, such a configuration using an "electric environment" as described above has the advantage that the electrical circuit needs only to be connected to one single capacitor element (on which the (capacitor) electrodes are disposed, i.e. the "second" capacitor element). If the electrical circuit is only connected to one single capacitor element (on which the (capacitor) electrodes are disposed, i.e. the "second" capacitor element) it is preferred that this is the fixed capacitor element. This has the advantage that the rotatable capacitor element can rotate "freely".

As used herein the term "capacitor element" refers to an element, which is in particular required to form a capacitor, i.e. one or more capacitor elements can form a capacitor. The minimum requirements for a capacitor are two electrically conductive elements (and a dielectric between them, which may simply be air). Accordingly, a capacitor element typically comprises at least one electrically conductive element.

As outlined above, the electrically conductive elements of the capacitor elements can have any shape, except for a circular shape with the vertical axis (i.e. the rotation axis) as center. Accordingly, the electrically conductive elements of the capacitor elements may have the shape of a spot, a quadrangle such as a square or a triangle, a circle (having a center which is not the rotation axis), a segment of a circle, or an ellipse. Most preferably the electrically conductive element(s) of the capacitor elements have essentially the shape of circle segments or blunt circle segments, for example as shown in FIG. 8A-D. It is also particularly preferred that the electrically conductive element(s) of the capacitor elements have essentially the shape of a triangle or quadrangle (e.g., a rectangle, square or trapezoid), for example as shown in FIG. 9.

One single electrically conductive element may comprise (or form) one or more (capacitor) electrodes. Preferably, one single electrically conductive element forms one single (capacitor) electrode.

Preferably, the electrically conductive elements comprise (more preferably they are made of) a material having an electric conductivity of at least $5.10^4$ S/m. Although such conductor materials include metals, electrolytes, superconductors, semiconductors, plasmas and some nonmetallic conductors such as graphite and conductive polymers, solid conductor materials are generally preferred for the electrically conductive element. Preferred examples of such solid conductor materials include metals (most preferably copper, silver and aluminium) and metal alloys; superconductor materials such as metallic superconductors (e.g. magnesium diboride), A15 phases (e.g. vanadium-silicon, vanadium-gallium, niobium-germanium, and niobium-tin), and ceramic and iron-based superconductors (e.g. $La_{1.85}Ba_{0.15}CuO_4$, and YBCO (Yttrium-Barium-Copper-Oxide)); semiconductors such as silicon, germanium, gallium arsenide, silicon carbide, gray tin, gray selenium, tellurium, boron nitride, boron phosphide, boron arsenide, and the like; and graphite. More preferably, the material comprised by the electrically conductive element (preferably, of which the electrically conductive element is made of) is a metal, a metal alloy, a metal-containing material such as conductive silver paste, graphite, graphene, a conductive polymer (e.g., polyaniline or doped polypyrrole), or a doped semiconductor with increased conductivity (e.g., phosphor-doped silicon or arsenic-doped germanium), or any combination thereof.

"At least one" fixed capacitor element means one or more fixed capacitor elements, however, exactly one single fixed capacitor element is preferred.

The rotatable capacitor element capable of rotating around the vertical axis (i.e. the axis around which a rotation is to be detected), whereas the at least one fixed capacitor element is fixed, i.e. stationary. To this end, the rotatable capacitor element can preferably be attached to a shaft of an apparatus for measuring the coagulation characteristics of a sample, which shaft is rotatable around the vertical axis (and preferably extends along the vertical axis), such that a rotation of the shaft causes a rotation of the rotatable capacitor element and/or vice versa. Preferably, the rotatable capacitor element has a "balanced" shape to enable steady rotation (i.e., without imbalance) around the vertical axis. The fixed capacitor element may then be attached to any stationary/immobile component of the apparatus, for example such that it is essentially in parallel to the rotatable capacitor element.

The rotatable capacitor element and the at least one fixed capacitor element are arranged such that the at least one electrically conductive element of the rotatable capacitor element faces the at least one electrically conductive element of the at least one fixed capacitor element. This means that in at least one rotation position of the rotatable capacitor element the at least one electrically conductive element of the rotatable capacitor element faces the at least one electrically conductive element of the fixed capacitor element. Preferably, in such a face-to-face rotation position, there is no (solid) element/component between the electrically conductive element of the capacitor elements facing each other. More preferably, in such a face-to-face rotation position, there is nothing (except air) between the electrically conductive element of the capacitor elements facing each other. Preferably, in such a face-to-face rotation position, the distance between the at least one electrically conductive element of the rotatable capacitor element and the at least one electrically conductive element of the fixed capacitor element does not exceed 10 mm, more preferably said distance does not exceed 7 mm, even more preferably said distance does not exceed 5 mm, and most preferably said distance does not exceed 3 mm.

Preferably, the at least one fixed capacitor element is arranged essentially in parallel to the rotatable capacitor element. As used herein, "essentially parallel" "essentially in parallel" and similar expressions do not only include an exactly parallel orientation, but also deviations (from exactly parallel) of up to 15°, more preferably up to 10°, even more preferably up to 8°, still more preferably up to 5° and most preferably up to 2°. Particularly preferably, the deviation (from exactly parallel) is up to 1°. Such deviations are tolerable, since they do not impair the capacitor functionality of the two capacitor elements. In view thereof, the angle between the two capacitor elements is preferably not changing over time. If the angle between the two capacitor elements changes over time (e.g., due to tilting during rotation), the more complex electrode geometries described below are preferred.

As outlined above, the electrical circuit is preferably connected to the at least one fixed capacitor element, in particular to the at least one electrically conductive element of the fixed capacitor element. Such a connection may be configured as a cable, wire or the like. More preferably, there is no cable or wire connection to the rotatable capacitor element. In this case, the fixed capacitor element comprises preferably at least two (capacitor) electrodes.

The electrical circuit typically comprises at least one voltage source, for example a frequency generator, and, preferably, a detector for detecting capacitance differences by corresponding charge fluctuations, for example a charge amplifier circuit (also referred to as "current integrator circuit"). Preferably, the electrical circuit further comprises one or more filters, e.g. low-pass filters, to reduce noise (i.e., to increase the signal-to-noise ratio), which is/are preferably arranged after the detector in the electrical circuit.

In a preferred embodiment, the voltage source provides an alternating voltage to at least two (capacitor) electrodes ("first" and "second" electrode) located on a first capacitor element (e.g., on the fixed capacitor element), thereby inducing charge fluctuations on both electrodes, and, due to a capacitor effect, also at a third (capacitor) electrode located on the same (e.g., fixed) capacitor element or on a different (second) capacitor element (e.g., on the rotatable capacitor element). For example, if said three capacitor electrodes are located on the same (e.g., fixed) capacitor element, the fluctuations on the third (capacitor) electrode depend on the electric environment around the two electrodes, to which voltage is provided. The electric environment changes significantly by rotating the conductive element(s) of the other (e.g. rotatable) capacitor element. The charge fluctuations on the third electrode may optionally be amplified by a charge amplifier. A detector connected to the third (capacitor) electrode (or to the amplifier, if present) can then detect charge fluctuations induced by the rotation. Preferably, the detector is a synchronized detector, which is capable to detect the charge fluctuations on the third (capacitor) electrode synchronously to the initial voltages provided to the first and second electrode. Thereby, two voltages $U_1$ and $U_2$ are generated, which may subsequently be optionally send through separated low-pass filters to reduce noise. Both (filtered or non-filtered) voltage signals, $U_1$ and $U_2$, allow calculation of a signal proportional to the angular displacement D of the rotatable capacitor element by $D=(U_1-U_2)/U_1+U_2)$. To provide this signal as recordable data stream, the initial signals $U_1$ and $U_2$ can optionally also be digitized in an ADC (analog/digital converter) and then further processed digitally.

Preferably, the electrically conductive elements have an area size of at least 25 mm$^2$, more preferably at least 35 mm$^2$, even more preferably at least 42 mm$^2$, and most preferably at least 50 mm$^2$. It is also preferred that the distance between the fixed and rotatable capacitor elements is no more than 2 mm, more preferably no more than 1.5 mm, even more preferably no more than 1 mm. It is also preferred that the excitation/detection voltage frequency is at least 1 kHz, preferably at least 2 kHz, more preferably at least 5 kHz. Thereby a rotation of the rotatable capacitor element around the vertical axis can be detected quickly and with high accuracy.

For example, if all three conditions are fulfilled, i.e. if the electrically conductive elements have an area size of at least 25 mm$^2$, the distance between the fixed and rotatable capacitor elements is no more than 2 mm, and if the excitation/detection voltage frequency is at least 1 kHz, the electrical circuit will be capable of detecting a rotation of the rotatable capacitor element around the vertical axis of at least +/−2° with an accuracy of at least 0.2° in a time frame of at most 5 seconds. This enables an accurate and optimal detection of variations in a rotation around a vertical axis as caused by blood coagulation. Accordingly, it is preferred that the electrical circuit is capable of detecting a rotation of the rotatable capacitor element around the vertical axis of at least +/−2° with an accuracy of at least 0.2° in a time frame of at most 5 seconds.

Preferably, (each of) the capacitor element(s) comprises
an electrically non-conductive support, which preferably extends essentially perpendicular to or along the vertical axis, and
the at least one electrically conductive element is disposed on the electrically non-conductive support.

As used herein, "essentially" perpendicular to or along includes deviations of up to 10°, more preferably up to 7°, even more preferably up to 5°, still more preferably up to 2° and most preferably up to 1°. For example, the capacitor element has preferably a plate-like, disk-like or cylindrical shape. In particular at least the rotatable capacitor element has preferably essentially a plate-like, disk-like or cylindrical shape.

Preferably the shape of the fixed capacitor element corresponds to the shape of the rotatable capacitor element. For example, if the rotatable capacitor element has a plate-like or a disk-like shape also the fixed capacitor element has preferably a plate-like or a disk-like shape. Preferred exemplified embodiments of such capacitive detection means, wherein the capacitor elements have plate-like or disk-like shapes are shown in FIGS. 4, 5, 6, 8A-D, and 11. For example, if the rotatable capacitor element has a cylindrical shape, the fixed capacitor element has the shape of a (partial) hollow cylinder, which surrounds the cylindrical rotatable capacitor element at least partially—or vice versa (i.e. the fixed capacitor element has a cylindrical shape and the rotatable capacitor element has the shape of a (partial) hollow cylinder). A preferred exemplified embodiment of such capacitive detection means, wherein the rotatable capacitor element has a cylindrical shape and the fixed capacitor element has the shape of a (partial) hollow cylinder, is shown in FIG. 9.

The electrically non-conductive support material of the capacitor elements is preferably a lightweight material, which has preferably less than 2.5 g/cm$^3$ mass density. Preferably a capacitor element weighs no more than 20 g, more preferably no more than 15 g and most preferably no more than 10 g. More preferably, the capacitive detection means have a weight of 100 g or less, more preferably of 50 g or less, even more preferably of 25 g or less and most preferably of 15 g or less.

Preferably, the electrically non-conductive support material of the capacitor elements is selected from PCB (printed circuit board) material known in the art (e.g., fibre-enforced epoxy polymer or phenolic resin), plastic, ceramic, glass or carbon fiber.

The electrically conductive element is preferably disposed on the electrically non-conductive support by photochemical coating, sputtering, metal evaporation, or screen printing.

If more than one electrically conductive element is comprised by a capacitor element, the more than one electrically conductive elements are preferably insulated from each other and from (all) other parts of the capacitive detection means. This can be achieved for example by implementing the conductive elements as thin layers on non-conductive materials or by embedding the conductive elements into non-conductive material.

Preferably, the at least one fixed capacitor element comprises a sine oscillator electrode (S), a cosine oscillator electrode (C), and/or a pickup electrode (P). As used herein, a "sine oscillator electrode (S)" is an electrode, which is connected to an alternating voltage with frequency f, while a "cosine oscillator electrode (C)" is an electrode, which is connected to another alternating voltage of similar or nearly similar frequency f' and a phase shift of 900 compared to f. As used herein, a "pickup electrode (P)" is an electrode, which is coupled to S and C by electric fields and receives charge fluctuations according to the alternating voltages at S and C.

For example, the fixed capacitor element may preferably comprise three kinds of electrodes: one or more sine oscillator electrodes (S), one or more cosine oscillator electrodes (C), and one or more pickup electrodes (P). The S and C electrodes can then preferably be connected to an (oscillating) voltage, e.g. to a rectangular oscillating voltage with a 90°-phase shift between S and C. Depending on the shape and/or position of the conductive element, for example on the rotatable capacitor element, the capacitance $C_{SP}$ from electrode S to electrode P and the capacitance $C_{CP}$ from electrode C to electrode P may then be changed in opposite directions. Accordingly, the actual angle of the conductive element on the rotatable capacitor element (relative to the conductive element on the fixed capacitor element) may then be calculated from the difference of $C_{SP}$ and $C_{CP}$ after scaling to the sum of $C_{SP}$ and $C_{CP}$. Such a configuration provides a high insensitivity to external mechanical distortions like distance changes, vibrations, tilting of the axis, and the like.

In a preferred embodiment the electrical circuit is capable of generating an electrical voltage signal that is proportional to the angular displacement between the (isolated) conductive element(s) on the rotatable capacitor element and the fixed capacitor element. To this end, the fixed capacitor element preferably comprises one or more S, P and C electrodes, which are preferably arranged in an alternating manner, for example in the order S-P-C or in the order C-P-S. The electrical circuit comprises a frequency generator, which preferably provides alternating electrode voltages at S and C, thereby inducing charge fluctuations on both electrodes, and, due to the capacitor effect via one or more conductive element(s) on the rotatable capacitor element, also at electrode P. Thereby, the fluctuations on P depend on the electric environment around the electrodes S and C, which changes significantly during rotation of the conductive element(s) on the rotatable capacitor element. Preferably, direct capacitive charge variations at electrode P inducible without the "loop way" over said one or more conductive element(s) on the rotatable capacitor element are minimized by additional grounded electrodes located between electrodes S and P, and between electrodes C and P, respectively, on the fixed capacitor element. Preferably, the electrical circuit further comprises a charge amplifier, which is capable of amplifying said charge fluctuations on electrode P. Preferably, the electrical circuit also comprises a synchronized detector, which is capable of detecting the (amplified charge fluctuations on electrode P) synchronously to the initial alternating voltages at electrodes S and C. In this way, two voltages $U_S$ and $U_C$ can be generated. Preferably, the electrical circuit further comprises two low-pass filters, through which the two voltages $U_S$ and $U_C$ can be send separately (i.e. each voltage to a separate low-pass filter) to reduce noise. Both resulting voltage signals, $U_S$ and $U_C$, allow calculation of a signal proportional to the angular displacement D of the rotatable capacitor element by $D=(U_S-U_C)/U_S+U_C)$. The electrical circuit may further comprise an ADC (analog/digital converter) in order to digitize the $U_S$ and $U_C$ signals and to provide those signals as recordable data stream, which may then be further processed digitally.

Other configurations of the array of conductive electrodes on the fixed capacitor element are also conceivable without changing the above described general measurement principle. For example, one sine oscillator electrode (S) may be combined on the fixed capacitor element with two pickup electrodes (P1 and P2), e.g. at each side of S, which may preferably be separated by ground electrodes to prevent directly induced charge fluctuations without the loop way via the rotatable conductive element. In this case, the angular movement of said conductive element results in charge increase at one of the two pickup electrodes and in charge decrease at the other pickup electrode.

Preferably, the capacitor element comprises more than one electrically conductive elements and/or more than one (capacitor) electrodes, for example 2, 3, 4, 5, 6, 7, 8, 9, 10, 11, 12, 13, 14, 15, 16, 17, 18, 19 or 20 or even more than 20 electrically conductive elements and/or 2, 3, 4, 5, 6, 7, 8, 9, 10, 11, 12, 13, 14, 15, 16, 17, 18, 19 or 20 or even more than 20 (capacitor) electrodes. Preferably, the capacitor element comprises two electrically conductive elements and/or two (capacitor) electrodes. Preferably, the capacitor element comprises three electrically conductive elements and/or three (capacitor) electrodes. Preferably, the capacitor element comprises four electrically conductive elements and/or four (capacitor) electrodes. Preferably, the capacitor element comprises five electrically conductive elements and/or five (capacitor) electrodes. Preferably, the capacitor element comprises six electrically conductive elements and/or six (capacitor) electrodes. Preferably, the capacitor element comprises seven electrically conductive elements and/or seven (capacitor) electrodes. Preferably, the capacitor element comprises eight electrically conductive elements and/or eight (capacitor) electrodes. Preferably, the capacitor element comprises nine electrically conductive elements and/or nine (capacitor) electrodes. Preferably, the capacitor element comprises ten electrically conductive elements and/or ten (capacitor) electrodes. Preferably, the capacitor element comprises eleven electrically conductive elements and/or eleven (capacitor) electrodes. Preferably, the capacitor element comprises twelve electrically conductive elements and/or twelve (capacitor) electrodes. Preferably, the capacitor element comprises thirteen electrically conductive elements and/or thirteen (capacitor) electrodes. Preferably, the capacitor element comprises fourteen electrically conductive elements and/or fourteen (capacitor) electrodes. Preferably, the capacitor element comprises fifteen electrically conductive elements and/or fifteen (capacitor) electrodes. Preferably, the capacitor element comprises sixteen electrically conductive elements and/or sixteen (capacitor) electrodes. Preferably, the capacitor element comprises seventeen electrically conductive elements and/or seventeen (capacitor) electrodes. Preferably, the capacitor element comprises eighteen electrically conductive elements and/or eighteen (capacitor) electrodes. Although the above numbers refer in particular to the sum of all electrically conductive elements and/or of all (capacitor) electrodes present on one single capacitor element, the numbers exclude in particular ground electrodes, if present. In general, the higher the number of electrically conductive elements/(capacitor) electrodes, the less sensitive the detection means for undesired interferences impairing measurement accuracy, such as tilting of the shaft.

Preferably, the at least one fixed capacitor element comprises one single sine oscillator electrode (S), one single cosine oscillator electrode (C), and one single pickup electrode (P). More preferably, the one single sine oscillator electrode (S), the one single cosine oscillator electrode (C), and the one single pickup electrode (P) are disposed on the support in an alternating manner, for example in the order S-P-C or in the order C-P-S. In this case, the rotatable capacitor element comprises preferably one single conductive element. An exemplified embodiment of such a configuration is shown in FIG. 8A.

Preferably, the at least one fixed capacitor element comprises at least two sine oscillator electrodes (S), at least two cosine oscillator electrodes (C), and at least two pickup electrodes (P). More preferably, the at least two sine oscillator electrodes (S), the at least two cosine oscillator electrodes (C), and the at least two pickup electrodes (P) are disposed on the support in an alternating manner, for example in the order S-P-C//S-P-C etc. or in the order C-P-S//C-P-S etc. In this case, the rotatable capacitor element comprises preferably at least two conductive elements, which are preferably evenly distributed on the rotatable capacitor element, for example two conductive elements positioned opposite to each other (180°). Accordingly, the groups of one S electrode, one C electrode and one P electrode are preferably arranged on the fixed capacitor element in a corresponding manner, i.e. also evenly distributed, for example two groups of one S electrode, one C electrode and one P electrode are positioned opposite (180°) to each other. An exemplified embodiment of such a configuration is shown in FIG. 8B.

Preferably, the at least one fixed capacitor element comprises at least three sine oscillator electrodes (S), at least three cosine oscillator electrodes (C), and at least three pickup electrodes (P). More preferably, the at least three sine oscillator electrodes (S), the at least three cosine oscillator electrodes (C), and the at least three pickup electrodes (P) are disposed on the support in an alternating manner, for example in the order S-P-C//S-P-C//S-P-C etc. or in the order C-P-S//C-P-S//C-P-S etc. In this case, the rotatable capacitor element comprises preferably at least three conductive elements, which are preferably evenly distributed on the rotatable capacitor element, for example three conductive elements positioned in a 120° angle to each other. Accordingly, the groups of one S electrode, one C electrode and one P electrode are preferably arranged on the fixed capacitor element in a corresponding manner, i.e. also evenly distributed, for example three groups of one S electrode, one C electrode and one P electrode are positioned in a 120° angle to each other. An exemplified embodiment of such a configuration is shown in FIG. 8C.

Preferably, the at least one fixed capacitor element comprises at least four sine oscillator electrodes (S), at least four cosine oscillator electrodes (C), and at least four pickup electrodes (P). More preferably, the at least four sine oscillator electrodes (S), the at least four cosine oscillator electrodes (C), and the at least four pickup electrodes (P) are disposed on the support in an alternating manner, for example in the order S-P-C//S-P-C//S-P-C//S-P-C etc. or in the order C-P-S//C-P-S//C-P-S//C-P-S etc. In this case, the rotatable capacitor element comprises preferably at least four conductive elements, which are preferably evenly distributed on the rotatable capacitor element, for example four conductive elements positioned in a 90° angle to each other. Accordingly, the groups of one S electrode, one C electrode and one P electrode are preferably arranged on the fixed capacitor element in a corresponding manner, i.e. also evenly distributed, for example four groups of one S electrode, one C electrode and one P electrode are positioned in a 90° angle to each other.

Preferably, the at least one fixed capacitor element comprises at least five sine oscillator electrodes (S), at least five cosine oscillator electrodes (C), and at least five pickup electrodes (P). More preferably, the at least five sine oscillator electrodes (S), the at least five cosine oscillator electrodes (C), and the at least five pickup electrodes (P) are disposed on the support in an alternating manner, for example in the order S-P-C//S-P-C//S-P-C//S-P-C//S-P-C etc. or in the order C-P-S//C-P-S//C-P-S//C-P-S//C-P-S etc. In this case, the rotatable capacitor element comprises preferably at least five conductive elements, which are preferably evenly distributed on the rotatable capacitor element, for example five conductive elements positioned in a 72° angle to each other. Accordingly, the groups of one S electrode, one C electrode and one P electrode are preferably arranged on the fixed capacitor element in a corresponding manner, i.e. also evenly distributed, for example five groups of one S electrode, one C electrode and one P electrode are positioned in a 72° angle to each other.

Preferably, the at least one fixed capacitor element comprises at least six sine oscillator electrodes (S), at least six cosine oscillator electrodes (C), and at least six pickup electrodes (P). More preferably, the at least six sine oscillator electrodes (S), the at least six cosine oscillator electrodes (C), and the at least six pickup electrodes (P) are disposed on the support in an alternating manner, for example in the order S-P-C//S-P-C//S-P-C//S-P-C//S-P-C//S-P-C etc. or in the order C-P-S//C-P-S//C-P-S//C-P-S//C-P-S//C-P-S etc. In this case, the rotatable capacitor element comprises preferably at least six conductive elements, which are preferably evenly distributed on the rotatable capacitor element, for example six conductive elements positioned in a 60° angle to each other. Accordingly, the groups of one S electrode, one C electrode and one P electrode are preferably arranged on the fixed capacitor element in a corresponding manner, i.e. also evenly distributed, for example six groups of one S electrode, one C electrode and one P electrode are positioned in a 60° angle to each other. An exemplified embodiment of such a configuration is shown in FIG. 8D.

As described above, the at least one fixed capacitor element preferably comprises at least one ground electrode located between the different types of electrodes (e.g., S, C, and P electrodes or S, P1 and P2 electrodes), for example (i) between a sine oscillator electrode (S) and a pickup electrode (P); and/or (ii) between a cosine oscillator electrode (C) and a pickup electrode (P).

In a third aspect, the present invention also provides a capacitive detection means for detecting variations in a rotation around a vertical axis caused by blood coagulation comprising
  a rotatable dielectric element, which is capable of rotating around the vertical axis and which does not have a circular shape with the vertical axis as center;
  two fixed capacitor elements; and
  an electrical circuit, preferably connected to a fixed capacitor element;
wherein each of the two fixed capacitor elements comprises at least one electrically conductive element; the two fixed capacitor elements are arranged such that the electrically conductive elements of the capacitor elements face each other; and the dielectric element is at least partially placed between the two fixed capacitor elements.

This capacitive detection means differs from the above described capacitive detection means (according to the second aspect of the present invention) in particular in that the rotatable element is not a capacitor element as described above, but a dielectric element, which is at least partially placed between two fixed capacitor elements. The functional principle is quite similar to the above described capacitive detection means according to the second aspect of the present invention: In general, the electrically conductive elements of the two fixed capacitor elements, which face each other (as described above in the context of the second aspect of the invention), function in a similar manner as the two conductive plates of a parallel-plate capacitor. To detect a rotation, a rotatable dielectric element is used, which is at least partially placed between the two fixed capacitor elements. By such an arrangement, a rotation of the rotatable dielectric element influences the capacitance formed by the two fixed capacitor elements. To this end, the rotatable dielectric elements can have any shape, except for a circular shape with the vertical axis (i.e. the rotation axis) as center. The reason is that a rotation (or a variation in the rotation)

can be detected by a variation in the capacitance (or by charge fluctuation), however, the rotation of an element having a circular shape with the rotation axis as center would not result in a variation in the capacitance (or by charge fluctuation).

Since the functional principle of the third aspect of the present invention is very similar to that of the second aspect of the present invention, most of the definitions and preferred embodiments outlined above for the second aspect also apply to the third aspect.

For example, the electrical circuit is generally as described above in the context of the second aspect. However, since according to the third aspect, two fixed capacitor elements are present, both comprising at least one electrically conductive element, the electrical circuit is preferably connected to both fixed capacitor elements, in particular to the at least one electrically conductive element of both fixed capacitor elements.

As used herein, the term "dielectric element" refers to an element comprising or consisting of a dielectric material. A dielectric material is an electrical insulator that can be polarized by an applied electric field. Preferably, the dielectric material is a solid dielectric material. Solid dielectrics are perhaps the most commonly used dielectrics in electrical engineering, and many solids are very good insulators. Some examples include porcelain, glass, and most plastics. Preferred solid dielectric materials are those used in the manufacture of capacitors. Preferred examples of a dielectric material include a polymer material, such as polyethylene (PE) or polytetrafluorethylene (PTFE); a ceramic material, such as steatite; a glass material, aluminium oxide; mica; silicon dioxide; and any combination thereof.

Preferably, the dielectric element has essentially a disk-like or plate-like shape, which preferably extends essentially perpendicular to the vertical axis. As used herein, "essentially" perpendicular includes deviations of up to 10°, more preferably up to 7°, even more preferably up to 5°, still more preferably up to 2° and most preferably up to 1°. As described above, the dielectric element may have any shape as long as it does not have a circular shape with the vertical axis as center. Accordingly, the dielectric element may have the shape of a quadrangle such as a square or a triangle, a circle (having a center which is not the rotation axis), a segment of a circle, or an ellipse. Preferably, the dielectric element has a "balanced" shape to enable steady rotation (i.e., without imbalance) around the vertical axis. For example, the dielectric element may have the shape of two (or more) oppositely arranged circle segments, triangles or quadrangles. A preferred exemplary embodiment thereof is shown in FIG. 10.

The rotatable dielectric element is capable of rotating around the vertical axis (i.e. the axis around which a rotation is to be detected), whereas the two fixed capacitor element are fixed, i.e. stationary. To this end, the rotatable dielectric element can preferably be attached to a shaft of an apparatus for measuring the coagulation characteristics of a sample, which shaft is rotatable around the vertical axis (and preferably extends along the vertical axis), such that a rotation of the shaft causes a rotation of the rotatable dielectric element and/or vice versa. The fixed capacitor elements may then be attached to any stationary/immobile component(s) of the apparatus, for example such that they are essentially in parallel to each other and to the rotatable dielectric element.

As described for the second aspect, the electrically conductive elements of the capacitor elements can have any shape, except for a circular shape with the vertical axis (i.e. the rotation axis) as center. Accordingly, the electrically conductive elements of the capacitor elements may have the shape of a spot, a quadrangle such as a square or a triangle, a circle (having a center which is not the rotation axis), a segment of a circle, or an ellipse. Most preferably the electrically conductive element(s) of the capacitor elements have essentially the shape of circle segments or blunt circle segments, for example as shown in FIG. 8A-D. It is also particularly preferred that the electrically conductive element(s) of the capacitor elements have essentially the shape of a triangle or quadrangle (e.g., a rectangle, square or trapezoid), for example as shown in FIG. 9.

One single electrically conductive element may comprise (or form) one or more (capacitor) electrodes. Preferably, one single electrically conductive element forms one single (capacitor) electrode.

Preferably, the electrically conductive elements comprise (more preferably they are made of) a material having an electric conductivity of at least $5 \cdot 10^4$ S/m. Although such conductor materials include metals, electrolytes, superconductors, semiconductors, plasmas and some nonmetallic conductors such as graphite and conductive polymers, solid conductor materials are generally preferred for the electrically conductive element. Preferred examples of such solid conductor materials include metals (most preferably copper, silver and aluminium) and metal alloys; superconductor materials such as metallic superconductors (e.g. magnesium diboride), A15 phases (e.g. vanadium-silicon, vanadium-gallium, niobium-germanium, and niobium-tin), and ceramic and iron-based superconductors (e.g. $La_{1.85}Ba_{0.15}CuO_4$, and YBCO (Yttrium-Barium-Copper-Oxide)); semiconductors such as silicon, germanium, gallium arsenide, silicon carbide, gray tin, gray selenium, tellurium, boron nitride, boron phosphide, boron arsenide, and the like; and graphite. More preferably, the material comprised by the electrically conductive element (preferably, of which the electrically conductive element is made of) is a metal, a metal alloy, a metal-containing material such as conductive silver paste, graphite, graphene, a conductive polymer (e.g., polyaniline or doped polypyrrole), or a doped semiconductor with increased conductivity (e.g., phosphor-doped silicon or arsenic-doped germanium), or any combination thereof.

Preferably, the two fixed capacitor elements are arranged in an essentially parallel manner (as described above) to each other and to the rotatable dielectric element. Preferably, the capacitor elements have essentially a plate-like or disk-like shape as described above: Preferably the shape of the fixed capacitor element corresponds to the shape of the rotatable capacitor element. For example, if the rotatable capacitor element has a plate-like or a disk-like shape also the fixed capacitor element has preferably a plate-like or a disk-like shape. Preferred exemplified embodiments of such capacitive detection means, wherein the capacitor elements have plate-like or disk-like shapes are shown in 10.

Preferably, the electrically conductive elements have an area size of at least 25 mm², more preferably at least 35 mm², even more preferably at least 42 mm², and most preferably at least 50 mm². It is also preferred that the distance between each of the fixed capacitor elements and the rotatable dielectric element is no more than 2 mm, more preferably no more than 1.5 mm, even more preferably no more than 1 mm. It is also preferred that the excitation/detection voltage frequency is at least 1 kHz, preferably at least 2 kHz, more preferably at least 5 kHz. Thereby a rotation of the rotatable capacitor element around the vertical axis can be detected quickly and with high accuracy.

For example, if all three conditions are fulfilled, i.e. if the electrically conductive elements have an area size of at least 25 mm², the distance between each of the fixed capacitor elements and the rotatable dielectric element is no more than 2 mm, and if the excitation/detection voltage frequency is at least 1 kHz, the electrical circuit will be capable of detecting a rotation of the rotatable capacitor element around the vertical axis of at least +/−2° with an accuracy of at least 0.2° in a time frame of at most 5 seconds. This enables an accurate and optimal detection of variations in a rotation around a vertical axis as caused by blood coagulation. Accordingly, it is preferred that the electrical circuit is capable of detecting a rotation of the rotatable capacitor element around the vertical axis of at least +/−2° with an accuracy of at least 0.2° in a time frame of at most 5 seconds.

Preferably, (each of) the capacitor element(s) comprises
an electrically non-conductive support, which preferably extends essentially perpendicular to the vertical axis, and
the at least one electrically conductive element is disposed on the electrically non-conductive support.

The electrically non-conductive support material of the capacitor elements is preferably a lightweight material, which has preferably less than 2.5 g/cm³ mass density. Preferably a capacitor element weighs no more than 20 g, more preferably no more than 15 g and most preferably no more than 10 g. More preferably, the capacitive detection means have a weight of 100 g or less, more preferably of 50 g or less, even more preferably of 25 g or less and most preferably of 15 g or less.

Preferably, the electrically non-conductive support material of the capacitor elements is selected from PCB (printed circuit board) material known in the art (e.g., fibre-enforced epoxy polymer or phenolic resin), plastic, ceramic, glass and carbon fiber.

The electrically conductive element is preferably disposed on the electrically non-conductive support by photochemical coating, sputtering, metal evaporation, or screen printing.

If more than one electrically conductive element is comprised by a capacitor element, the more than one electrically conductive elements are preferably insulated from each other and from (all) other parts of the capacitive detection means. This can be achieved for example by implementing the conductive elements as thin layers on non-conductive materials or by embedding the conductive elements into non-conductive material.

Preferably, the at least one fixed capacitor element comprises a sine oscillator electrode (S), a cosine oscillator electrode (C), and/or a pickup electrode (P) as described above, in the context of the second aspect.

Preferably, (i) the pickup electrode (P) and (ii) the sine oscillator electrode (S) and/or the cosine oscillator electrode (C) are located on distinct fixed capacitor elements. For example, the upper fixed capacitor element comprises a pickup electrode (P) and the lower fixed capacitor element comprises a sine oscillator electrode (S) and/or a cosine oscillator electrode (C). Alternatively, it is also preferred that the lower fixed capacitor element comprises a pickup electrode (P) and the upper fixed capacitor element comprises a sine oscillator electrode (S) and/or a cosine oscillator electrode (C). In this way, the grounded electrodes located in between the S or C and P electrodes are not required if the S/C electrode(s) and the P electrode(s) are located on distinct capacitor elements.

Preferably, a capacitor element comprises more than one electrically conductive elements and/or more than one (capacitor) electrodes, for example 2, 3, 4, 5, 6, 7, 8, 9, 10, 11, 12, 13, 14, 15, 16, 17, 18, 19 or 20 or even more than 20 electrically conductive elements and/or 2, 3, 4, 5, 6, 7, 8, 9, 10, 11, 12, 13, 14, 15, 16, 17, 18, 19 or 20 or even more than 20 (capacitor) electrodes as described above.

For example, it is preferred that (i) the upper capacitor element comprises one single pickup electrodes (P) and the lower capacitor element comprises one single sine oscillator electrodes (S) and/or one single cosine oscillator electrodes (C) or (ii) the upper capacitor element comprises one single sine oscillator electrodes (S) and one single cosine oscillator electrodes (C) and the lower capacitor element comprises one single pickup electrodes (P). Preferably, (i) the upper capacitor element comprises at least two pickup electrodes (P) and the lower capacitor element comprises at least two sine oscillator electrodes (S) and/or at least two cosine oscillator electrodes (C) or (ii) the upper capacitor element comprises at least two sine oscillator electrodes (S) and at least two cosine oscillator electrodes (C) and the lower capacitor element comprises at least two pickup electrodes (P). Preferably, (i) the upper capacitor element comprises at least three pickup electrodes (P) and the lower capacitor element comprises at least three sine oscillator electrodes (S) and/or at least three cosine oscillator electrodes (C) or (ii) the upper capacitor element comprises at least three sine oscillator electrodes (S) and at least three cosine oscillator electrodes (C) and the lower capacitor element comprises at least three pickup electrodes (P). Preferably, (i) the upper capacitor element comprises at least four pickup electrodes (P) and the lower capacitor element comprises at least four sine oscillator electrodes (S) and/or at least four cosine oscillator electrodes (C) or (ii) the upper capacitor element comprises at least four sine oscillator electrodes (S) and at least four cosine oscillator electrodes (C) and the lower capacitor element comprises at least four pickup electrodes (P). Preferably, (i) the upper capacitor element comprises at least five pickup electrodes (P) and the lower capacitor element comprises at least five sine oscillator electrodes (S) and/or at least five cosine oscillator electrodes (C) or (ii) the upper capacitor element comprises at least five sine oscillator electrodes (S) and at least five cosine oscillator electrodes (C) and the lower capacitor element comprises at least five pickup electrodes (P). Preferably, (i) the upper capacitor element comprises at least six pickup electrodes (P) and the lower capacitor element comprises at least six sine oscillator electrodes (S) and/or at least six cosine oscillator electrodes (C) or (ii) the upper capacitor element comprises at least six sine oscillator electrodes (S) and at least six cosine oscillator electrodes (C) and the lower capacitor element comprises at least six pickup electrodes (P).

It is also preferred that the oscillator electrodes (S), the cosine oscillator electrodes (C), and/or the pickup electrodes (P) are disposed on the support in an alternating manner, for example as described above, in the context of the second aspect. In particular, the sine oscillator electrodes (S) and the cosine oscillator electrodes (C) are preferably disposed on the support in an alternating manner.

In a further aspect, the present invention also provides an apparatus for measuring the coagulation characteristics of a sample comprising the capacitive detection means according to the present invention as described above, in particular according to the second and/or third aspect of the present invention. Thereby, the apparatus is preferably the apparatus according to the (first aspect) of the present invention as described herein. Accordingly, various preferred embodiments of (i) the capacitive detection means according to the present invention as described herein may be combined with various preferred embodiments of (ii) the apparatus according to the present invention as described herein. Preferred exemplary embodiments of such an apparatus according to the present invention comprising the capacitive detection means according to the present invention are shown in FIGS. 4 and 5.

Temperature Control Device

Viscoelastic measurements are preferably performed at body temperature, i.e. at about 37° C., in order to obtain meaningful results. To this end, it is preferred if the measurement apparatus comprises a temperature control device, which ensures that throughout the measurement the temperature of the sample, of the cup or of the cup receiving element is about 37° C. However, such temperature-controlled measurement setups are complicated to realize: Any (even flexible) wiring to a rotating cup induces unwanted counter forces, resulting in a decreased measuring accuracy. In view thereof, the present invention provides in a further aspect a contactless temperature control device which allows for contactless temperature sensing and heating/temperature control of the cup containing the blood sample. The temperature control device senses and regulates the temperature of the cup (and the blood sample contained therein) so as to achieve a certain temperature resembling or approaching body temperature of a patient, usually in the range between 32 and 39° C.

In a further aspect, the invention thus provides a temperature control device for controlling the temperature of a cup and/or of a cup receiving element while measuring the coagulation characteristics of a sample in a thromboelastic measurement apparatus comprising:
  a heating comprising an electromagnetic radiation emitting element emitting (thermal) radiation with an emission maximum in the wavelength range from 300 to 3,000 nm;
  a temperature sensing element for contactless measurement of (thermal) radiation in the wavelength range from more than 3,000 nm to 30,000 nm; and
  optionally, controlling means for activating or deactivating the heating depending on the temperature measured by the temperature sensing element having an accuracy of at least +/−3° C.

Currently available irradiative temperature sensing and heating devices used for contactless temperature control (e.g., so-called "pyrometers" basing on the pyro-electric effect, or photodiodes, phototransistors or photoresistors that are sensitive in the infra-red (IR) range of the electromagnetic spectrum) are not designed for use in the rather narrow spaces available in a viscoelastic measurement apparatus. The major problem within such narrow spaces results from the largely overlapping emission and detection ranges, for example from a direct interference of heating devices emitting in the IR range with temperature sensors detecting in the same IR range, in particular if both are placed within a short distance to each other and/or if they are well surrounded by reflecting (for example metallic) material: Even though the sensor may be directed at the cup and should measure only the cup temperature, the radiation emitted by the nearby heating is typically not sufficiently focused to avoid reflections from other surfaces that falsify the measurement of the exact cup temperature.

In contrast to other methods known in the art, the temperature control device according to the present invention minimizes such direct interference of an electromagnetic radiation source with a thermal radiation sensor by relying on spectral separation, or, in other words, segregation of heating wavelength and detecting wavelength. The present inventors found that sufficient spectral separation can be achieved by shifting the wavelength (range) used by the heating device to a lower wavelength range, namely 300-3,000 nm, while contactless thermal radiation sensors usable for temperature detection in the range between 20 and 50° C. employ a spectrum above 3,000 nm, usually up to 30,000 nm.

The temperature control device according to the present invention advantageously allows control and stabilization of the temperature of a blood sample tested in viscoelastic measurements at a predefined value (usually 37° C., but also lower or higher values) in case conventional ("wired") heating is impossible. Spectral separation of the wavelength emitted from the electromagnetic radiation emitting element used as a heating on the one hand, and the wavelength detected by the temperature sensor on the other hand enables placing the heating element and temperature sensor close together—which is advantageous in the narrow space available of viscoelastic measurement apparatuses. It further allows the heating and temperature sensor to be almost completely surrounded by reflective material.

As used herein, the term "thermal radiation" refers to electromagnetic radiation generated by the thermal motion of charged particles in matter. Accordingly, thermal radiation is the emission of electromagnetic waves from all matter that has a temperature greater than absolute zero. It represents a conversion of thermal energy into electromagnetic energy. Thermal radiation is different from thermal convection and thermal conduction. Examples of thermal radiation include the visible light and infrared light.

The temperature control device according to the present invention comprises a heating element comprising (or consisting of) an electromagnetic radiation emitting element emitting (thermal) radiation with its maximum of the spectral radiation distribution in the wavelength range from 300 to 3,000 nm. The electromagnetic radiation emitting element is thus a source of electromagnetic radiation with its maximum in the wavelength range from 300 nm to 3,000 nm (3 μm). Preferably, the total radiation energy emitted at wavelengths above 3 μm is less than 20% of the total radiation energy, more preferably it is less than 15%, even more preferably it is less than 10%, and still more preferably it is less than 5% of the total radiation energy. Most preferably, the electromagnetic radiation emitting element does essentially not emit electromagnetic radiation having a wavelength of more than 3,000 nm (3 μm).

More preferably, the electromagnetic radiation emitting element emits electromagnetic radiation having a wavelength in the wavelength range from 300 to 2,000 nm (2 μm). In this case it is preferred that the total radiation energy emitted at wavelengths above 2 μm is less than 20% of the total radiation energy, more preferably it is less than 15%, even more preferably it is less than 10%, and still more preferably it is less than 5% of the total radiation energy. Most preferably, the electromagnetic radiation emitting element does essentially not emit electromagnetic radiation having a wavelength of more than 2,000 nm (2 μm).

Even more preferably, the electromagnetic radiation emitting element emits electromagnetic radiation having a wavelength in the wavelength range from 300 to 1,500 nm (1.5 μm). In this case it is preferred that the total radiation energy emitted at wavelengths above 1.5 μm is less than 20% of the total radiation energy, more preferably it is less than 15%, even more preferably it is less than 10%, and still more preferably it is less than 5% of the total radiation energy. Most preferably, the electromagnetic radiation emitting element does essentially not emit electromagnetic radiation having a wavelength of more than 1,500 nm (1.5 µm).

Still more preferably, the electromagnetic radiation emitting element emits electromagnetic radiation having a wavelength in the wavelength range from 300 to 1,200 nm (1.2 µm). In this case it is preferred that the total radiation energy emitted at wavelengths above 1.2 µm is less than 20% of the total radiation energy, more preferably it is less than 15%, even more preferably it is less than 10%, and still more preferably it is less than 5% of the total radiation energy. Most preferably, the electromagnetic radiation emitting element does essentially not emit electromagnetic radiation having a wavelength of more than 1,200 nm (1.2 µm).

Most preferably, the electromagnetic radiation emitting element emits electromagnetic radiation having a wavelength in the wavelength range from 300 to 1,000 nm (1 µm). In this case it is preferred that the total radiation energy emitted at wavelengths above 1 µm is less than 20% of the total radiation energy, more preferably it is less than 15%, even more preferably it is less than 10%, and still more preferably it is less than 5% of the total radiation energy. Most preferably, the electromagnetic radiation emitting element does essentially not emit electromagnetic radiation having a wavelength of more than 1,000 nm (1 µm).

The advantage of an electromagnetic radiation emitting element emitting radiation in the wavelength range from 300 to 3,000 nm is that such radiation is distinguishable from the radiation emitted from elements having a temperature of 20-50° C. (for example body temperature). For example, it is well-known that humans (normal body temperature) radiate most strongly at a wavelength of about 10,000 nm (10 µm). Or, in more general, according to Planck's law for the spectral distribution of thermal radiation, a black body having a temperature of about 30-40° C. emits thermal radiation at a maximum of about 10 µm.

Furthermore, an electromagnetic radiation emitting element emitting radiation in the wavelength range from 300 to 3,000 nm is sufficient to maintain the temperature of the cup/cup receiving element at about body temperature when using simple and lower-cost light or IR diodes. Diodes, in particular lower-cost diodes, with a radiation maximum below 300 nm are not able to maintain the required temperature of the cup/cup receiving element, since the emission energy is too low. On the other hand, the radiation of diodes, in particular lower-cost diodes, emitting with a radiation maximum above 3000 nm strongly interferes with the thermal radiation of the cup/cup receiving element and therefore complicates the measurement of its exact temperature by remote sensing, if not even making it impossible.

Preferably, the electromagnetic radiation emitting element is an electromagnetic radiation emitting diode, such as an LED (light-emitting diode), a near-IR diode or a UV diode. As used herein, the term "LED" (light-emitting diode) includes anorganic light-emitting diodes (LED) as well as organic light emitting diodes (OLED). In general, diodes, such as LEDs, have the advantage that they are very small and can be easily used in the thromboelastic measurement apparatus. An LED typically has a wavelength maximum in the visible wavelength range, in particular from 450-780 nm. A "near-IR diode" differs from the above described LED in that it typically has a wavelength maximum in the near infrared (near-IR; NIR) wavelength range, in particular from 780 nm to 3,000 nm (3 µm). A "UV diode" differs from the above described LED in that it typically has a wavelength maximum in the ultraviolet (UV) wavelength range, in particular from 300 nm to 450 nm.

Preferably, the electromagnetic radiation emitting element is an LED having a wavelength maximum in the visible range of the spectrum (450-780 nm, e.g. 660 nm), or a NIR diode having a wavelength maximum in the near IR of the spectrum (780-3000 nm, e.g. 850 nm). In general, since the output power of a UV diode, an LED, or a near-IR emitting diode is typically increasing with the wavelength of the emission maximum, longer wavelengths of the radiation source may be more beneficial due to reduced costs of the required components. In view thereof NIR diodes are preferred electromagnetic radiation emitting elements. On the other hand, however, it is advantageous that the difference between the emission range (i.e. the wavelength range of the electromagnetic radiation emitting element) and the detecting/sensing range (i.e. the wavelength range of the temperature sensing element) is as large as possible. In view thereof, UV diodes and LEDs are preferred. Most preferably, the electromagnetic radiation emitting element provides a compromise between the above outlined requirements, for example the electromagnetic radiation emitting element is a NIR diode emitting in the range of 800-1200 nm, for example about 850 nm.

The temperature control device according to the present invention comprises a temperature sensing element for contactless measurement of thermal radiation in the wavelength range from more than 3,000 nm to 30,000 nm. Thereby, wires and the like connecting the temperature sensing element with the (rotatable cup/cup receiving element) are avoided. As described above, it is the major goal of the temperature sensing element to detect whether or not the cup/cup receiving element has the desired temperature, which is usually in the range of 20° C.-50° C., preferably 30° C.-40° C., and most preferably about 37° C. (body temperature). According to Planck's radiation law a black body having a temperature in the above specified ranges emits at a wavelength maximum of 9-10 µm (9,000-10,000 nm), which is well within the detection range of 3,000-30,000 nm. Accordingly, the temperature sensing element is able to detect temperatures in the desired range. On the other hand, such a detection range is sufficiently distinct from the wavelength emission maxima of the electromagnetic radiation emitting element as described above.

Preferably, the temperature sensing element for contactless measurement of thermal radiation has a (maximum) sensitivity in the wavelength range of 4,000-30,000 nm. More preferably, the temperature sensing element for contactless measurement of thermal radiation has a (maximum) sensitivity in the wavelength range of 5,000-25,000 nm. Even more preferably, the temperature sensing element for contactless measurement of thermal radiation has a (maximum) sensitivity in the wavelength range of 5,000-25,000 nm. Still more preferably, the temperature sensing element for contactless measurement of thermal radiation has a (maximum) sensitivity in the wavelength range of 6,000-20,000 nm. Most preferably, the temperature sensing element for contactless measurement of thermal radiation has a (maximum) sensitivity in the wavelength range of 7,000-15,000 nm.

Preferably, the temperature sensing element is a pyroelectric detector, a photoresistor, or a photodiode.

A pyro-electric detector is an infrared sensitive optoelectronic component which is typically used for detecting electromagnetic radiation in a wavelength range from 3 to 14 µm. A pyroelectric detector is a thermal detector, whereby temperature fluctuations produce a charge change on the surface of pyroelectric crystals, which produces a corresponding electrical signal. There are different pyroelectric materials available, three of which are commonly used in pyroelectric detectors: DLaTGS, LiTaO$_3$, and PZT.

A photoresistor (or light-dependent resistor, LDR, or photocell) is a light-controlled variable resistor. A photoresistor is usually made of a high resistance semiconductor. In the dark, a photoresistor can have a resistance as high as several megohms (MΩ), while in the light, a photoresistor can have a resistance as low as a few hundred ohms. If incident light on a photoresistor exceeds a certain frequency, photons absorbed by the semiconductor give bound electrons enough energy to jump into the conduction band. The resulting free electrons (and their hole partners) conduct electricity, thereby lowering resistance. In summary, the resistance of a photoresistor decreases with increasing incident light intensity; in other words, it exhibits photoconductivity. A photoresistor can thus be applied in light-sensitive detector circuits. Preferred photoresistors include Lead sulphide (PbS) and indium antimonide (InSb) LDRs (light-dependent resistors) and Ge:Cu photoconductors.

A photodiode is a semiconductor device that converts light into current. The current is generated when photons are absorbed in the photodiode. A small amount of current is also produced when no light is present. Photodiodes using a PIN junction rather than a p-n junction are preferred due to their increased response speed. Preferred examples of photodiodes include lead(II)sulphide diodes, mercury cadmium telluride diodes, and, most preferably, cadmium telluride diodes.

The temperature controlling device according to the present invention optionally comprises controlling means for activating or deactivating the heating depending on the temperature measured by the temperature sensing element, which has preferably an accuracy of at least +/−3° C. For example, this can be achieved by using a sensing element with a proven accuracy of less than 2° C. and by an electrical control circuit that is fast enough to start or stop heating within seconds after a temperature deviation of +/−1° C. has been detected. To achieve double accuracy, the temperature deviation trigger can be for example reduced to +/−0.5° C. and a sensing element with proven accuracy of +/−1° C. can be used.

Such controlling means are an optional feature, since the control may also be performed manually by the user. For example, the temperature sensing element may be connected to a display and/or to an alarm, informing the user about the actual temperature and/or whether the actual temperature falls below the desired temperature, such that the user may then activate the heating. However, it is more convenient and, thus, preferred that the temperature controlling device according to the present invention comprises controlling means for activating or deactivating the heating depending on the actual temperature. To this end, the user may enter a desired temperature or the desired temperature may be given, e.g., by the measurement apparatus, for example by certain measurement programs. The controlling means can then compare the actual temperature as detected by the temperature sensing element with the desired temperature and activate the heating, if the actual temperature falls below the desired temperature or deactivate the heating if the desired temperature was reached. To this end, the controlling means is connected with (i) the temperature sensing element and (ii) the heating of the temperature controlling device.

In other words, the controlling means function in principle like a simple control loop, wherein the actual temperature is compared with the desired temperature and, if both values are identical the heating is deactivated, whereas if the actual temperature is below the desired temperature, the heating is activated.

In a further aspect, the present invention also provides an apparatus for measuring the coagulation characteristics of a sample comprising the temperature control device according to the present invention as described above. Preferably, such an apparatus also comprises the capacitive detection means according to the present invention as described above, in particular according to the second and/or third aspect of the present invention. Thereby, the apparatus is preferably the apparatus according to the (first aspect) of the present invention as described herein. Accordingly, various preferred embodiments of (i) the temperature control device according to the present invention as described herein; (ii) the capacitive detection means according to the present invention as described herein; and/or (iii) the apparatus according to the present invention as described herein may be combined. A preferred exemplary embodiment of an apparatus according to the present invention comprising temperature controlling device according to the present invention and the capacitive detection means according to the present invention are shown in FIG. 11.

In such an apparatus for measuring the coagulation characteristics of a sample comprising the temperature control device according to the present invention as described above the heating, in particular the electromagnetic radiation emitting element, preferably targets the shaft and/or the cup receiver. In general, it is most difficult to directly target the cup or the sample without interfering with the blood clotting process. The shaft and/or the cup receiver are typically of metal or metallic material, such that they provide a good thermal conductivity to the cup, and they are in close vicinity to the cup and the sample, such that almost no thermal energy is lost.

Preferably, in such an apparatus, the surface of the shaft and/or of the cup receiver, which is targeted by the electromagnetic radiation emitted from the heating, is dark and/or roughened. Thereby, absorption of the electromagnetic radiation emitted from the heating can be maximized. More preferably, the surface of the shaft and/or of the cup receiver, which is targeted by the electromagnetic radiation emitted from the heating, is black and/or roughened.

It is also preferred in such an apparatus that the distance between the heating, in particular the electromagnetic radiation emitting element, and the targeted shaft and/or cup receiving element is no more than 100 mm, more preferably no more than 80 mm, even more preferably no more than 75 mm, still more preferably no more than 60 mm, and most preferably no more than 50 mm. It is also preferred that the distance between the temperature sensing element and the targeted shaft and/or cup receiving element is no more than 100 mm, more preferably no more than 80 mm, even more preferably no more than 75 mm, still more preferably no more than 60 mm, and most preferably no more than 50 mm.

In a further aspect, the present invention also provides the use of the temperature control device according to the present invention as described above in measuring the coagulation characteristics of a sample, which is preferably a blood sample.

Method for Measuring Coagulation Characteristics

In a further aspect, the present invention provides a method for measuring the coagulation characteristics of a sample by means of an apparatus according to the present invention as described above, the method comprising the following steps:

(a) measuring variations in the rotation around the vertical axis by means of the detection means;
(b) converting said measured rotation/variation values to clot firmness values (CFV) of a viscoelastic measurement curve by the following formula:

$$CFV = (A_0 - A) * 100 / A_0$$

wherein $A_0$ is the difference between maximum and minimum signal at the two turning points of the oscillatory movement before measurement start, and A is the difference between maximum and minimum signal at the two turning points of the oscillatory movement at a certain time point during the measurement; and
(c) plotting the CFV's over the corresponding time points to obtain a measurement graph.

An exemplified measurement graph, which can be obtained by the method according to the present invention, namely in step (c) of the method according to the present invention, is shown in FIG. 3. Such a measurement graph provides for example information about the clotting time (CT), the clot formation time (CFT), the maximum clot firmness (MFT) and maximum lysis. One of the most important parameters is the clotting time (CT), i.e. the time between the time points of (i) (chemically induced) start of blot clotting and (ii) the formation of the first long fibrin fibers (indicated by the firmness signal exceeding a defined value). Another important parameter is the clot formation time (CFT), i.e. the time required for the clot firmness to increase from 4 to 20 mm. The CFT thus gives a measure for the velocity of the blood clot formation. The maximum clot firmness a (MCF), i.e. the maximum firmness achieved by a blood clot during measurement is also of great diagnostic importance. Further parameters obtainable from thromboelastographic measurement curves include the amplitude (A) at a certain time after CT (e.g., A10 is the amplitude 10 minutes after CT) and the lysis index (LI) in percent of amplitude reduction when compared to MCF at a certain time after CT (e.g., LI45 is the ratio between A45 and MCF in percent).

Preferably, for the measurement of variations in the rotation around the vertical axis the capacitive detection means according to the present invention as described above are used. Thereby, preferred embodiments of such a measurement by using the capacitive detection means as outlined above are also preferred in the context of the measurement method.

Furthermore, it is preferred that during the measurement a desired temperature, for example in the range of 20-50° C., preferably 30-40° C. and most preferably about 37° C., is achieved and maintained, for example by means of a temperature control device according to the present invention as described herein.

It may also be preferred—in particular if the apparatus is placed in a cold environment—that an additional step of pre-heating is included. In such a pre-heating step an (external) heating (for example one, two or more thermos-resistors providing e.g. 5 W power in total) may be used to pre-heat non-movable surrounding metal parts of the apparatus (to a desired temperature, e.g., to 37° C.). Such pre-heating by use of an (external) heating may be controlled by a conventional (commercially available) thermos-regulation unit comprising thermo-resistors and a thermocouple as sensor. This has the advantage that the desired temperature is quickly achieved and the temperature control device according to the present invention may then serve for maintaining the desired temperature during measurement.

BRIEF DESCRIPTION OF THE DRAWINGS

In the following a brief description of the appended figures will be given. The figures are intended to illustrate the present invention in more detail. However, they are not intended to limit the subject matter of the invention in any way.

DETAILED DESCRIPTION OF THE INVENTION

In the following, the present invention is illustrated in various exemplary embodiments. However, the present invention shall not to be limited in scope by the specific embodiments described in the following. The exemplary embodiments are given to enable those skilled in the art to more clearly understand and to practice the present invention. The present invention, however, is not limited in scope by the exemplary embodiments, which are intended as illustrations of selected aspects of the invention only, and methods which are functionally equivalent are within the scope of the invention. Indeed, various modifications of the invention in addition to those described herein will become readily apparent to those skilled in the art from the foregoing description, accompanying figures and the exemplary embodiments below. All such modifications fall within the scope of the appended claims.

Figure 4:
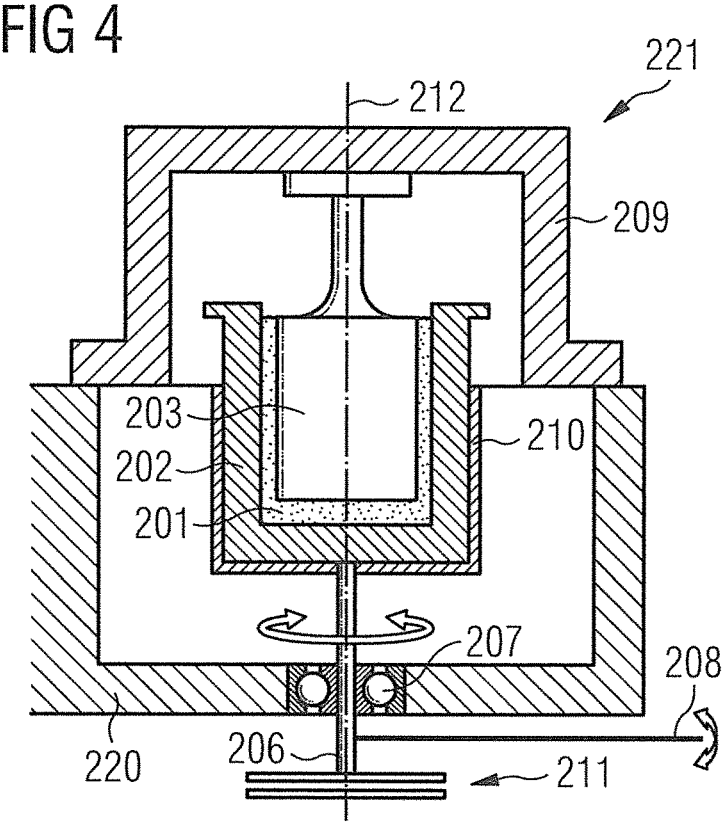
FIG. 4 is a schematic drawing of an apparatus according to a first preferred exemplary embodiment of the present invention.

FIG. 4 shows a schematic drawing of an apparatus (221) according to a first preferred exemplary embodiment of the present invention ("rotating cup" embodiment). According to this embodiment shown in FIG. 4, the apparatus (221) for measuring the coagulation characteristics of a sample (201), in particular a "test liquid", preferably blood (or elements/ components, comprises a cup (202) for receiving said sample. Furthermore, the apparatus comprises a pin (203), which can be placed inside the cup (202). In contrast to prior art measurement technologies, in the apparatus shown in FIG. 4 the pin (203) is—preferably detachably—fixed during the measurement regarding all spatial orientations/directions. This means in particular that the pin (203) cannot move in any direction. This is an important difference to the prior-art technologies described in FIG. 1 and FIG. 2: In the apparatus (21) shown in FIG. 1 the pin (3) is mounted via a wire (4) and can thus move in nearly any direction within the cup (2), which makes the measurement sensitive for shock or vibration. In the prior-art technology described in FIG. 2, the pin (103) is rotatable around the central vertical axis of the shaft (106).

In the first preferred exemplary embodiment shown in FIG. 4 the pin (203) can be for example fixed by attaching it to a cover (209). The cover (209) itself may for example be fixed, e.g. mounted, to a part of the apparatus, e.g. to a base support member (220), such as a base plate. Another possibility to fix the pin is to provide pin and cover in one piece (which includes both, pin and cover) and to attach that pin/cover piece directly to a base support member, such as a base plate. Preferably, said cup and pin are made of a polymeric material, which polymer preferably includes (meth)acrylic and/or styrene monomers, e.g. PMMA, MABS, ABS, PS, or any mixed co-polymer thereof.

According to the first preferred exemplary embodiment shown in FIG. 4, the cup (202) is rotatable, in particular around its vertical rotation axis (212). Preferably, the cup (202) is not movable along the axis (212), but only rotatable around axis (212). The rotation is enabled by providing a cup receiving element (210), which is connected to a shaft (206) and which is rotatable mounted into a base support member (220), such as a base plate, e.g., by at least one bearing (207). Similar to the cup (202), also the cup receiving element (210) is preferably not movable along the axis (212), but only rotatable around axis (212). In particular, a complete (full) rotation of 3600 around axis (212) is not even required—typically a small angular movement ("partial" rotation; circular motion) of, for example, +/−2.5° around axis (212) (i.e., in both directions) is sufficient for viscoelastic testing. Such a (partial) rotation is driven by an elastic coupling element (208), such as a spring wire, attached to the shaft (206), for example above or below said bearing (207).

During coagulation testing the blood sample typically forms a blood clot. After formation of the clot between cup (202) (e.g., a cuvette) and pin (203), the clot itself is stretched by the movement of the cup (202) relative to the pin (203). The detection of the characteristic parameters of the clot is based on the mechanical coupling of cup (202) and pin (203) by the clot. During a viscoelastic measurement, the pin (203) is fixed and the cup (202) rotates gently and slowly around the axis (212) by means of the elastic coupling element (208) and the cup receiving element (210). The movement of the cup (202) can be measured by various methods, for example by means of capacitive detection means (211), such as capacitor plates. In operation, the pin (203) is stationary and the rotatable shaft (206) and cup (202) placed in the cup receiver (210) are rotated back and forth by the elastic element (208, e.g. a spring wire), for example in an angular range of about ±5°. The rotation is transmitted by the coupling of the shaft (206) to the cup receiving element (210). When the blood clot forms an increasing torque acts against the oscillating movement of the cup (202), such that the cup/cup receiving element is oscillating in a decreased angular range of <±5°. This decrease in angular (oscillating) movement can be detected by suitable detection means (211) disposed below the pin (203) and cup (202)/cup receiving element (210).

This first preferred exemplary embodiment shown in FIG. 4 allows filling of the cup (202) with reagent and sample while being placed in the (optionally temperature-controlled) measurement position. It further avoids the need to attach a separate cup holder with cup and sample to the measurement device after filling the sample into the cup and before measurement start (as for example described in U.S. Pat. No. 5,777,215). Additionally, the first preferred exemplary embodiment shown in FIG. 4 further avoids the need to put the pin onto a small shaft before the measurement procedure starts (as for example described in U.S. Pat. No. 6,537,819 B2). Both improvements result in easier handling for the user and reduce in this way the risk for potential user mistakes.

Figure 1:
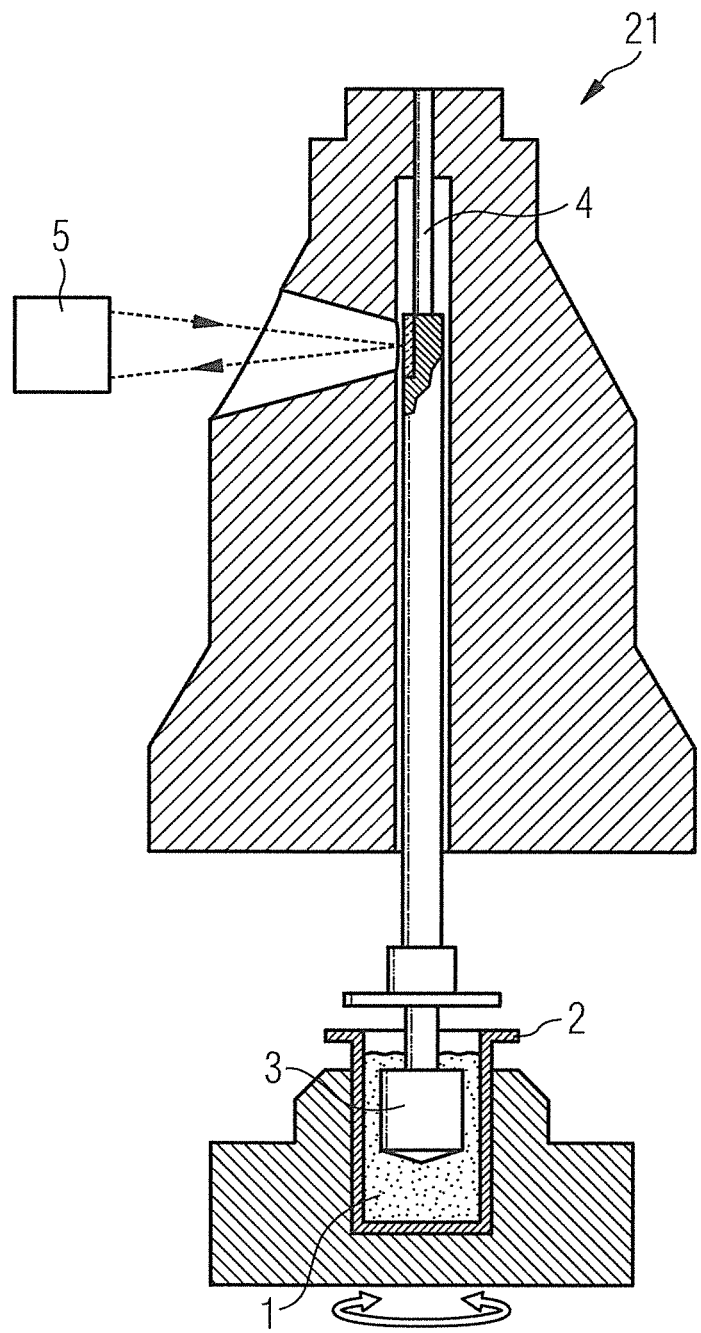
FIG. 1 is a schematic drawing of the measurement principle for early viscoelastic testing devices with optical detection means.

Another advantage of the first preferred exemplary embodiment shown in FIG. 4 is that the lower end of the shaft (206) can also be used for a movement detection unit, enabling new options of movement detection technologies (in addition to the prior art optical detection as shown in FIG. 1). For example, in the first preferred exemplary embodiment shown in FIG. 4, field-based detection by means of capacitive detection means (211), such as capacitor plates, e.g. in an oscillatory circuit, may be employed. Nevertheless, also a movement detection by light beam deflection would be still applicable in this first embodiment.

In contrast to the existing measurement technologies, in the preferred embodiment shown in FIG. 4 the pin is (optionally detachably) fixed and thus essentially immobile in all orientations. This is in contrast to prior-art apparatuses (see FIG. 1 and FIG. 2), where pin can either move in any direction (cf. FIG. 1 where the pin (3) is mounted via a spring wire (4)) or is rotatable around the vertical axis (cf. FIG. 2). This novel design according to the present invention has the advantage of allowing the filling of the cup with reagent and sample while being placed in its measurement position and at the measurement temperature. It thus avoids the filling of the cup outside of the measurement apparatus (and at a different temperature) and subsequently placing it in its measurement position (e.g. as described in U.S. Pat. No. 5,777,215). It is also obviates the need to mount the pin to a pin neck prior to measurement (e.g. as described U.S. Pat. No. 6,537,819). Thus, the apparatus enables easier handling and thereby reduces the risk for potential usage errors. Another advantage of this embodiment is that the distal end of the shaft is free and can be used for an alternative detection technology, in particular, for capacitive detection as described herein.

Figure 5:
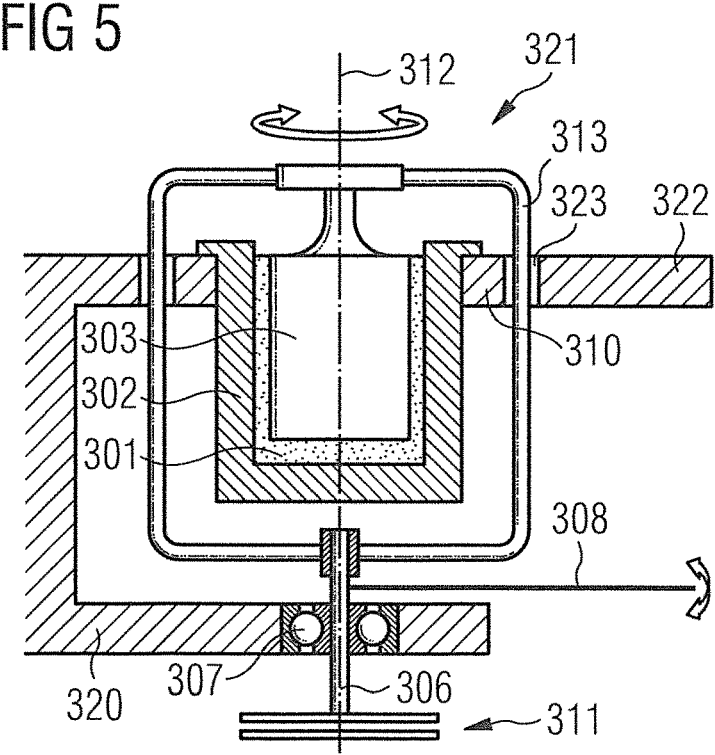
FIG. 5 is a schematic drawing of an apparatus according to a second preferred exemplary embodiment of the present invention.

FIG. 5 shows a schematic drawing of an apparatus (321) according to a second preferred exemplary embodiment of the present invention ("rotating pin" embodiment). According to this embodiment shown in FIG. 5, the cup (302) is now (preferably detachably) fixed, e.g. to a base plate, by means of a cup receiving element (310). This means in particular that the cup (302) cannot move in any direction. However, the pin (303) is rotatable, in particular around its vertical rotation axis (312). Preferably, the pin (303) is not movable along the axis (312), but only rotatable around axis (312). Again, in particular a complete (full) rotation of 3600 around axis (312) is not even required—typically a small angular movement ("partial" rotation; circular motion) of, for example, +/−4° around axis (312) (i.e., in both directions) is sufficient for viscoelastic testing. For example, the pin (303) can be (preferably detachably) fixed to a frame (313), which is connected to a shaft (306) and which is rotatable mounted into a base support member (320), such as a base plate, e.g., by at least one bearing (307). The frame (313) can be formed, for example, by an essentially rectangular arrangement of rods or tubes, e.g. comprising two or, more preferably, four metal rods or tubes, or by an essentially rectangular formed (single) rod or tube, which extends through corresponding openings (323) in the upper plate (322). The openings (323) in the upper plate (322) are preferably shaped such that they allow for an partial rotation/angular movement of the frame (313) of at least +/−2°, more preferably at least +/−4°. Similar to the embodiment shown in FIG. 4, the (partial) rotation (here: of the frame and, thus, the pin) is enabled by an elastic coupling element (308), such as a spring wire, attached to the shaft (306), which is connected to the frame (313). The elastic coupling element (308) can be mounted above or below said bearing (307).

Figure 2:
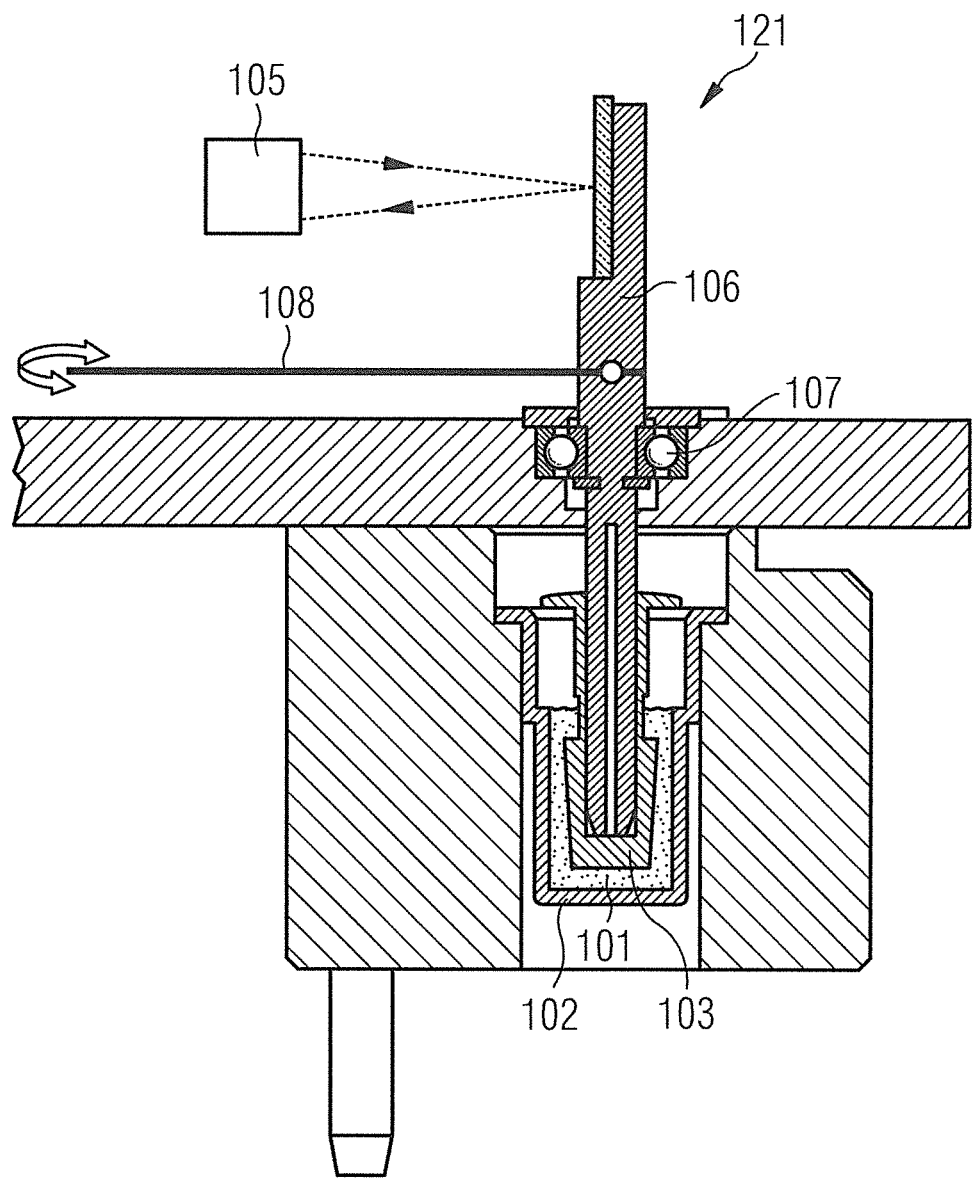
FIG. 2 is a schematic drawing of the measurement principle for viscoelastic testing devices with reduced sensitivity to environmental distortions like vibrations or shocks and with optical detection means.
Figure 3:
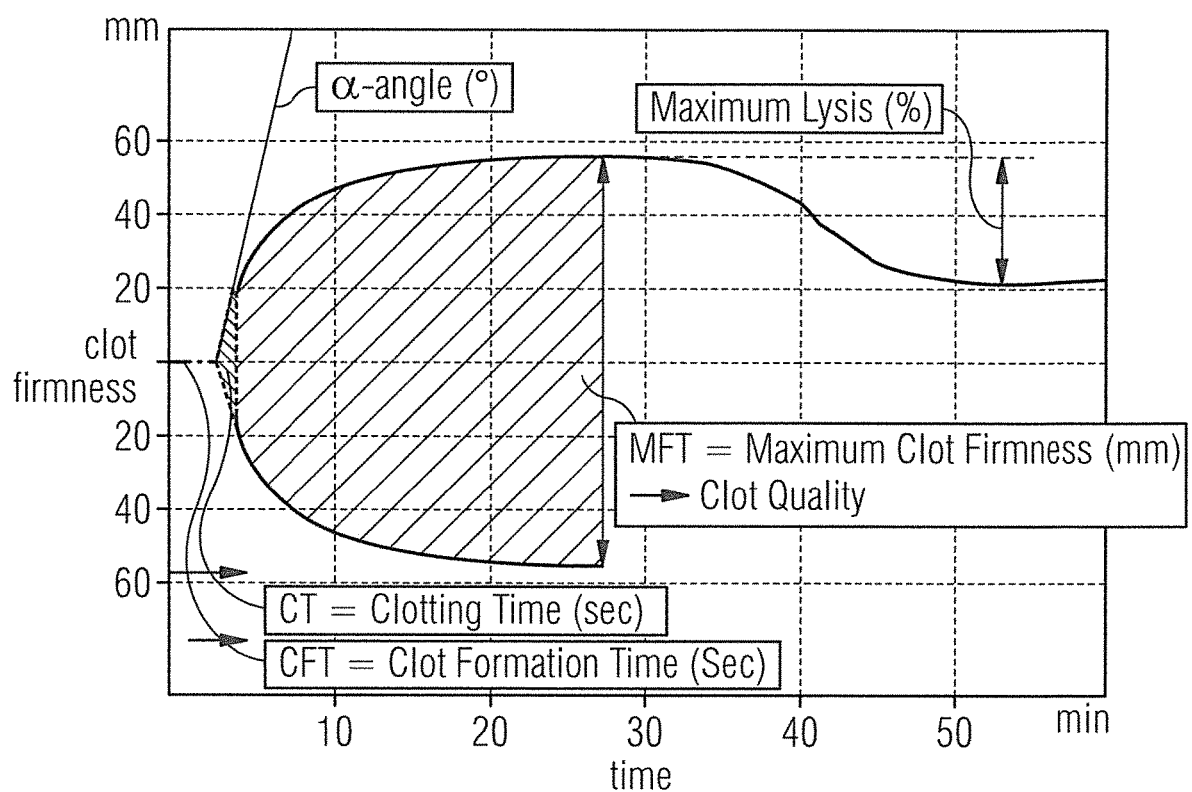
FIG. 3 is an exemplary diagram showing a typical thromboelastometric measurement.

Thus, in contrast to the prior art apparatus shown in FIG. 2, in the second preferred exemplary embodiment of the present invention shown in FIG. 5 rotatable fixing of the pin (303) is not realized by a shaft that is supported by a bearing above the cup/cup receiving element, but by a frame (313) attached to a shaft (306) that is supported by a bearing (307) below the cup/cup receiving element. In this way, the sample (301) can be filled into the cup (302) while being placed in the final measurement position—whereas in measurement apparatuses of the prior art, e.g. as described in U.S. Pat. No. 5,777,215, the bearing is positioned directly above the cup, which makes filling of the cup in the measurement position impossible. Moreover, due to the provision of the rotating means, such as the ball bearing, below the cup/cup receiving element (instead of above), the center of mass of the entire apparatus is considerably lower and, thus, the apparatus is less susceptible to vibrations, tilting, and similar environmental influences, which may otherwise influence the measurement.

In addition, the placement of the rotation means, such as the bearing (307) and/or the spring (308) below the cup/cup receiving element enables new movement detection means due to the resulting available space at the lower end of the shaft (306), similarly to the embodiment in FIG. 4. Accordingly, movement of the pin may be detected by optical means as described in the prior art (see FIG. 2) or by field-based detection by means of capacitive detection means (311), such as capacitor plates, e.g. in an oscillatory circuit.

In summary, also the second embodiment of the present invention as depicted in FIG. 5, realizes the three advantages mentioned above for the first embodiment as shown in FIG. 4, namely, (i) it allows filling of the cup (302) with the sample (and, optionally reagents) while being placed in the measurement position; (ii) it avoids the need to attach a separate cup holder, which holds the cup receiving element in measurement position after addition of the sample; and (iii) it enables the use of new movement detection means, such as capacitor plates. In addition, the apparatus' center of mass is considerably lower making the apparatus more robust and more easy to handle.

Figure 6:
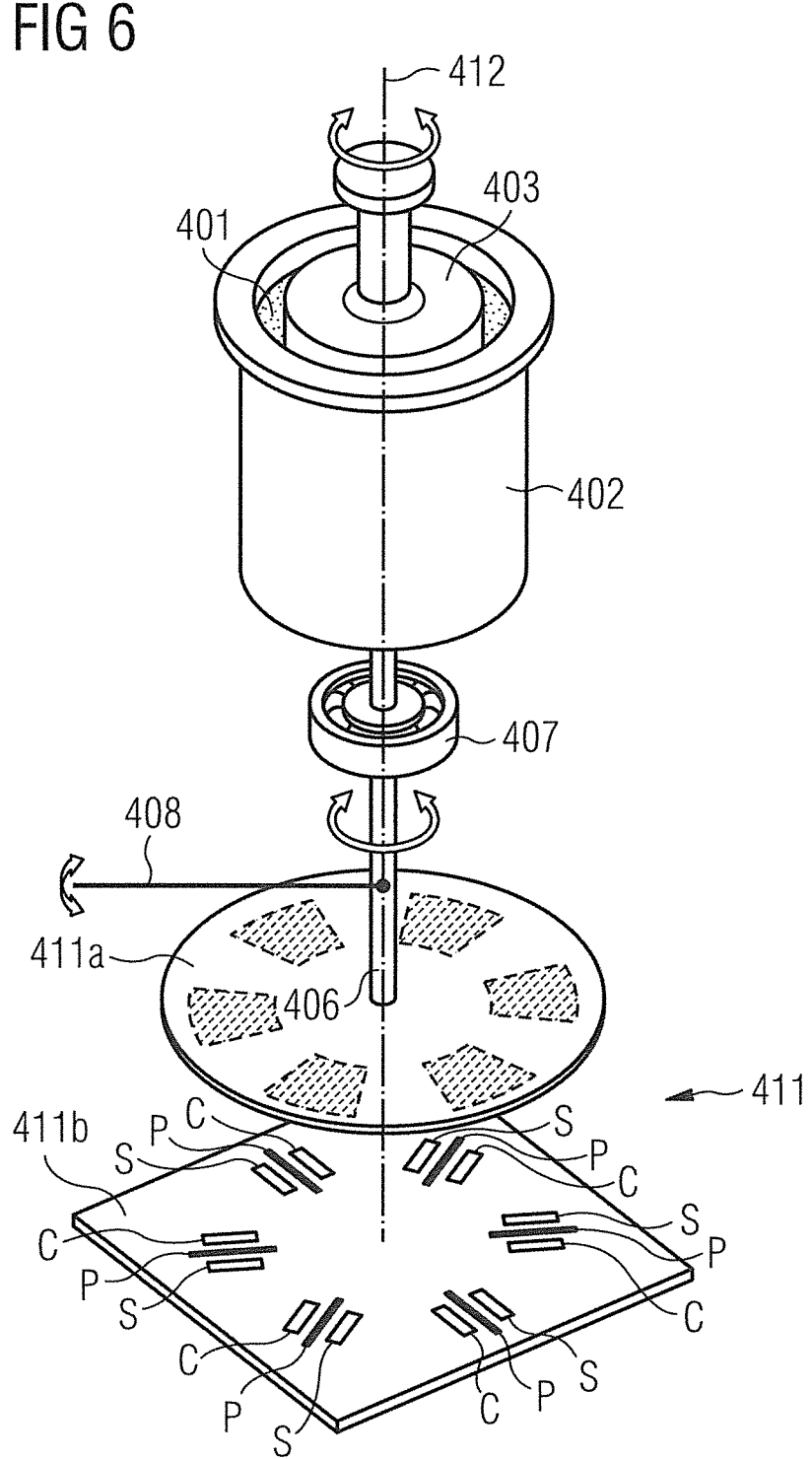
FIG. 6 is a schematic drawing of a movement detection system according to a preferred exemplary embodiment of the present invention.

FIG. 6 shows a preferred embodiment of the detection system according to the present invention, which may be used in viscoelastic measurements and which can be easily combined with the apparatus according to the present invention, for example with the preferred exemplified embodiment thereof shown in FIG. 4 or with the preferred exemplified embodiment thereof shown in FIG. 5. FIG. 6 shows schematically a cup (402) with a sample (401) and a pin (403). Below the cup (402) is a bearing (407) and a shaft (406), to which an elastic coupling element (408) is attached for providing rotation. The lower end of the shaft (406) is connected to a rotatable capacitor element (411a), which is preferably light-weight. Most preferably, the capacitor element (411a) is a disk. It is also preferred that the rotatable capacitor element (411a), in particular the disk, is rotational symmetric to facilitates rotation of the rotatable capacitor element (411a).

Preferably, the rotatable capacitor element (411a) is attached to the lower end of the shaft (406), such that shaft (406) is essentially perpendicular to the rotatable capacitor element (411a). The rotatable capacitor element (411a) has electrically conductive elements (shaded areas in the capacitor element (411a) shown in FIG. 6), which are preferably arranged in an rotationally symmetric manner. Said capacitor element (411a) can be obtained, for example, from standard PCB (printed circuit board) material, or from special lightweight PCB material known in the art, e.g. by etching the corresponding electrically conductive elements out of the conductive layer of the PCB material. Alternatively, said rotatable capacitor element (411a) can be obtained by applying a metal coating onto a support material, e.g., ceramics (for example by screen printing using a "mask" to obtain electrically conductive elements).

In parallel to the rotatable capacitor element (411a) another capacitor element (411b) is provided. In general, a capacitor element refers in particular to one or more conductive elements arranged on a support. Said capacitor element (411b) can also be obtained by, for example, etching PCB material or by applying metal to a support material, such as ceramics. Said capacitor element (411b) is fixed, while the rotatable capacitor element (411a) follows the rotating movement of shaft (406). In other words, rotatable capacitor element (411a) typically rotates with the rotating shaft. Said fixed capacitor element (411b) is electrically connected to a circuitry, while the conductive elements on rotatable capacitor element (411a) are electrically insulated from all other parts and from each other. The movement of the shaft (406) can thus be detected by the relative movement of the capacitor element (411a) (which rotates with shaft (406)) in respect to the fixed capacitor element (411b).

The fixed capacitor element (411b) may for example comprise three kinds of electrodes: Sine oscillator (S), Cosine oscillator (C), and Pickup electrode (P). The electrodes S and C can then be connected to a rectangular oscillating voltage with a 90°-phase shift between S and C. Other phase shifts and/or a frequency shift between the two signals are also possible. Depending on the angular position of shaft (406) and the corresponding exact position of the conductive element on the connected disk, the capacitance $C_{SP}$ from electrode S to electrode P and the capacitance $C_{CP}$ from electrode C to electrode P is changed in opposite directions. Accordingly, the actual angle of the rotatable conductive element can be calculated from the difference of $C_{SP}$ and $C_{CP}$ after scaling to the sum of $C_{SP}$ and $C_{CP}$. This scaling provides high insensitivity to external mechanical distortions like distance changes, vibrations, tilting of the axis, and the like.

Figure 7:
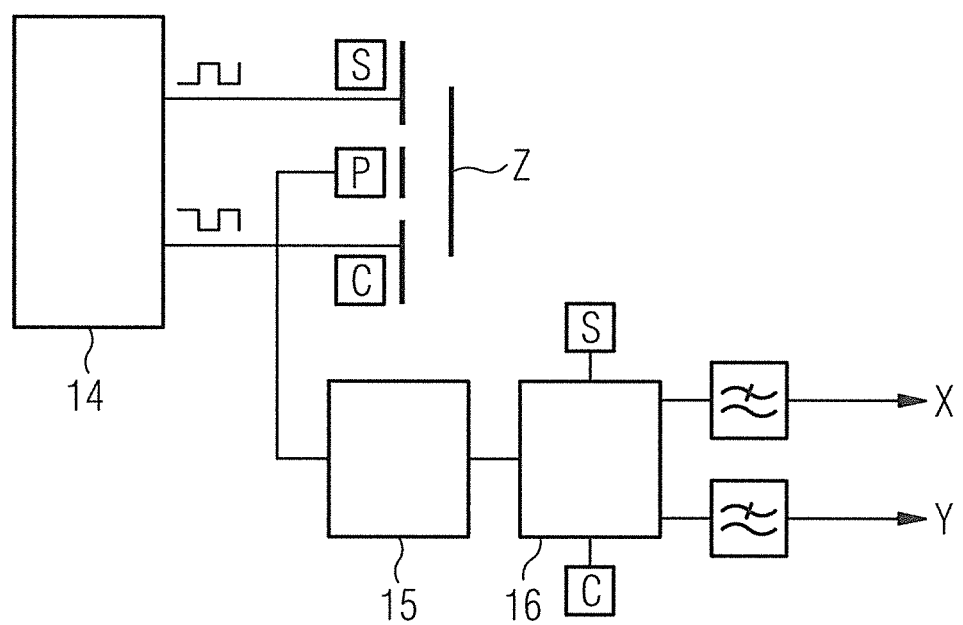
FIG. 7 is a schematic drawing of an electrical circuit that creates an electrical detection signal from the movement detection system of FIG. 6.

FIG. 7 shows schematically a preferred exemplary embodiment of a circuitry forming an oscillating circuit to measure capacitance differences between the electrodes S and C and the pickup electrode P. Electrodes "S", "C", and "P" are electrically conductive elements of the fixed electrode, whereas "Z" represents an electrically conductive element of the rotatable capacitor element. In this way, an electrical voltage signal can be generated that is proportional to the angular displacement between the isolated conductive layers on the rotatable capacitor element (411a) and the fixed capacitor element (411b), e.g. shown in FIG. 6: The alternating electrode voltages at S and C as provided by a frequency generator (14) induce charge fluctuations on both electrodes, and, due to the capacitor effect, also at electrode P. Thereby, the fluctuations on P depend on the electric environment around the electrodes S and C, which changes significantly by rotating the conductive element(s) Z on said disk. In particular, direct capacitive charge variations at P inducible without the loop way over said conductive elements can optionally be minimized by additional grounded electrodes between electrodes S and P, and between electrodes C and P, respectively.

Said charge fluctuations on electrode P can be amplified by a charge amplifier (15) and detected synchronously to the initial alternating voltages at electrodes S and C in a synchronized detector (16). In this way, two voltages $U_S$ and $U_C$ are generated and subsequently send through separated low-pass filters to reduce noise. Both resulting voltage signals, X and Y, allow calculation of a signal proportional to the angular displacement D of the capacitor element (11a) by $D=(X-Y)/(X+Y)$. To provide this signal as recordable data stream, the initial signals X and Y could be also digitized in an ADC (analog/digital converter) and then further processed digitally.

Other configurations in the fixed array of conductive electrodes are also conceivable without changing the general measurement principle. For example, one sine oscillator electrode (S) could be combined with two pickup electrodes (P1 and P2) at each side of S, separated again by ground electrodes to prevent directly induced charge fluctuations without the loop way via the rotatable conductive elements. In this case, the angular movement of said conductive elements would result in charge increase at one of the two pickup electrodes and in charge decrease at the other pickup electrode.

Figure 8A:
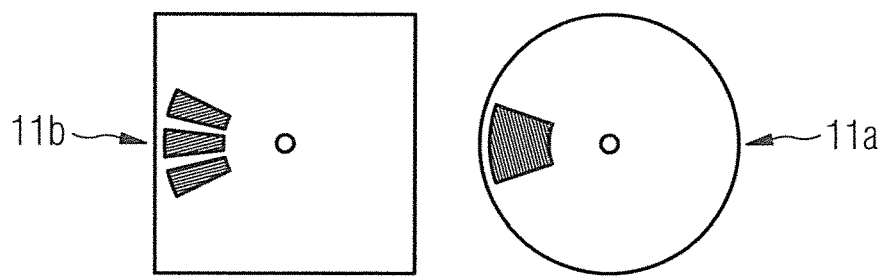
FIG. 8 is a schematic drawing of alternative electrode arrangements regarding number and symmetry.
Figure 8B:
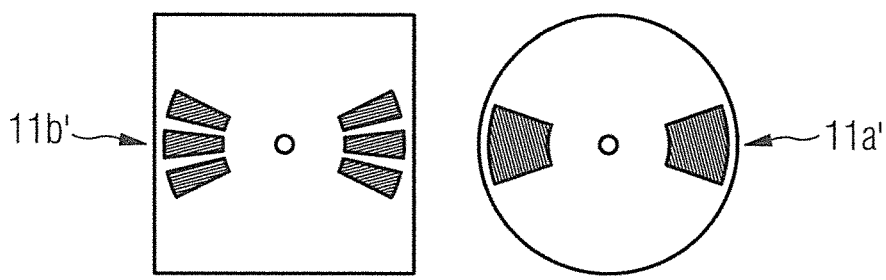
Figure 8C:
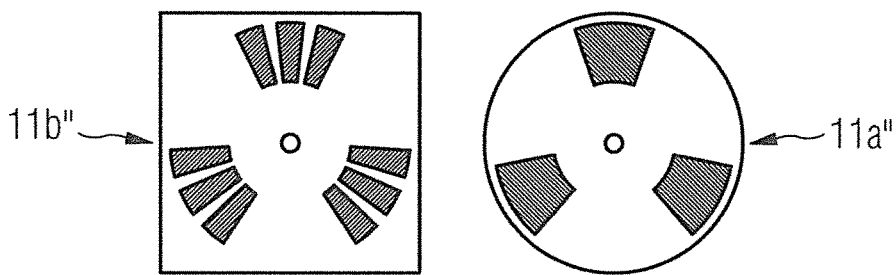
Figure 8D:
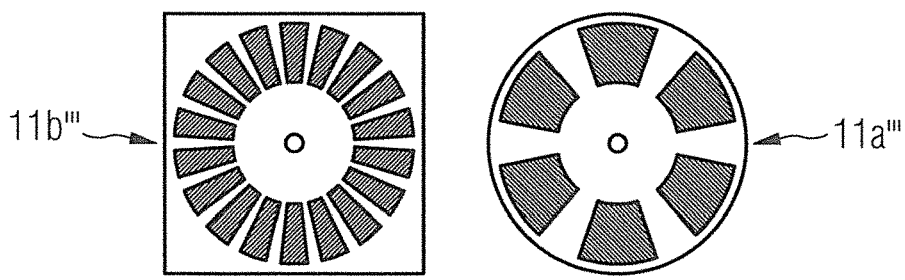

FIG. 8A-D shows preferred exemplary embodiments of the arrangement of the electrodes on the rotatable capacitor element (11a, 11a', 11a'', 11a'''; left) and on the fixed capacitor element (11b, 11b', 11b'', 11b'''; right). The exemplary embodiment shown in FIG. 8A represents the simplest approach of electrode arrangement. Such an arrangement may be sensitive to even slight tilting of the shaft holding the rotatable electrodes. The exemplary embodiment shown in FIG. 8B is insensitive to tilting of the shaft in one direction (i.e., tilting in the directions where the electrodes are placed), but not insensitive to tilting in other directions. The exemplary embodiment shown in FIG. 8C is the simplest approach that is insensitive to tilting of the shaft in any possible direction parallel to the electrodes plane. However, electrodes cover not yet all of the available space on the rotating disk. The exemplary embodiment shown in FIG. 8D is insensitive to shaft tilting in any direction and makes use of nearly all available space on the rotating disk for electrodes. This approach increases the resulting signal and considerably improves therefore the signal to noise ratio of the setup.

In summary, there is a high variability in number, arrangement and symmetry of employed electrodes. As a general principle, the precision and insensitivity against external distortions is improved by increasing the electrode number for each type S, C, and P from 1 to at least 3.

Figure 9:
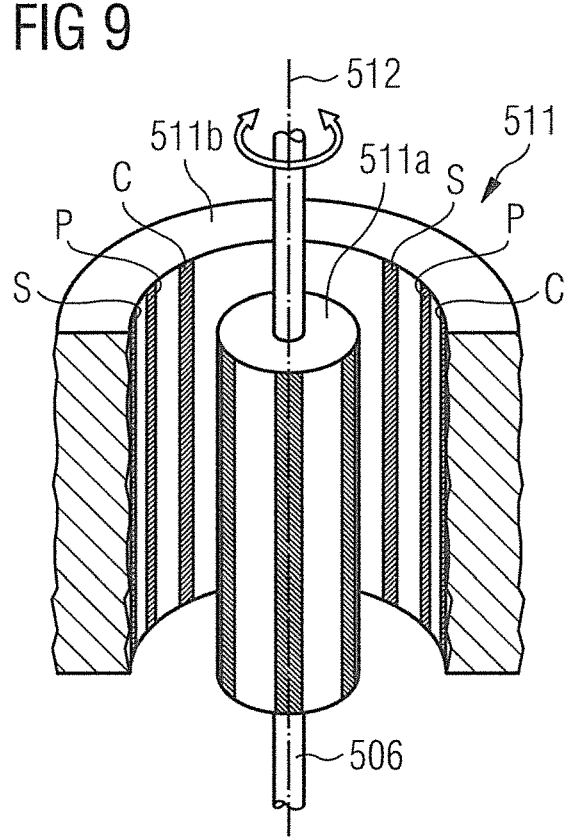
FIG. 9 is a schematic drawing of an alternative electrode arrangement according to a preferred exemplary embodiment of the present invention.

FIG. 9 shows another preferred exemplary embodiment of the capacitor elements (511a, 511b) of a detection system according to the present invention, wherein the capacitor elements (511a, 511b) have a cylindrically shaped geometry.

In cylindrical geometry, the conductive elements can be for example directly printed (or metal-evaporated) on a rotating, nonconductive shaft (506) to save weight. Alternatively, another cylindrical element serving as rotatable capacitor element (511a) may be attached to the shaft (506), for example a sleeve made of non-conductive material. Electrodes of type S, C and P are placed at a fixed position surrounding the rotating axis (512). The number of electrodes is again variable.

Figure 10:
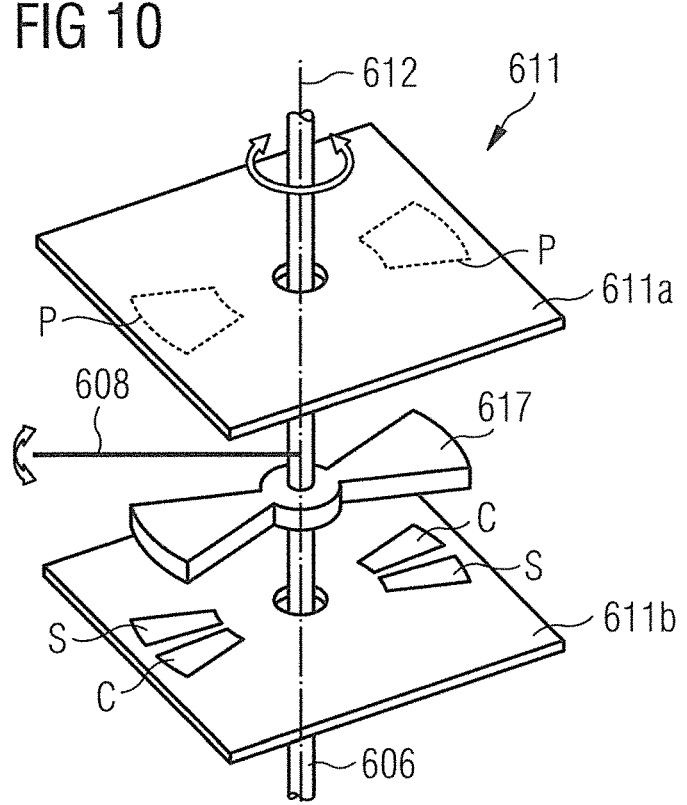
FIG. 10 is a schematic drawing of an alternative electrode arrangement according to a further preferred exemplary embodiment of the present invention.

FIG. 10 shows another preferred exemplary embodiment of the detection system according to the present invention, wherein the dielectric variation of the capacitance between fixed capacitor elements (611a, 611b) is used. Instead of using a rotating capacitor element relative to a fixed capacitor element to induce variations in capacitance as described above, in the present exemplary embodiment the electrodes S and C are aligned face-to-face to an electrode P in fixed positions. In this setup, the axis (612) is equipped with a segmented disk made of a dielectric material (617) that moves between the electrodes in dependence of the angular orientation of the axis. The dielectric material can be for example a polymer material like polyethylene (PE) or polytetrafluorethylene (PTFE), a ceramic material like steatite, or another dielectric material like aluminum oxide, mica, or silicon dioxide.

Figure 11:
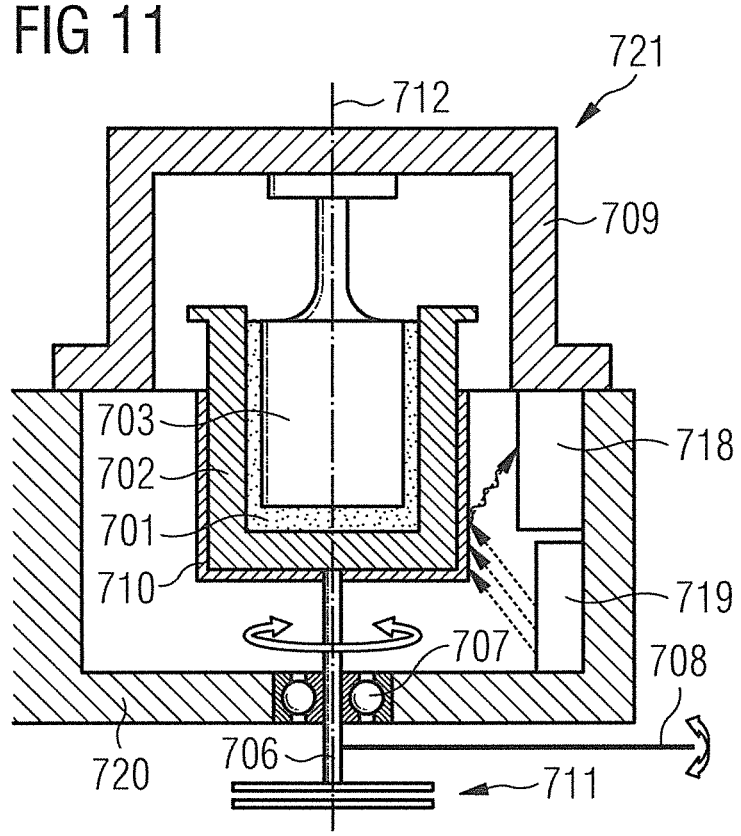
FIG. 11 is schematic drawing of a combination of preferred exemplary embodiments of the present invention.

FIG. 11 shows a schematic drawing of an apparatus (721) according to a preferred exemplary embodiment of the present invention equipped with a temperature control device (718, 719) according to the present invention. In general, the apparatus (721) corresponds to the preferred exemplary embodiment shown in FIG. 4 (see above), however, additionally equipped with a temperature control device (718, 719). Accordingly, the apparatus (721) comprises a cup (702) with a sample (701), which is attached to a cup receiving element (710). The immobile pin (703) is fixed to a cover (709). The cup receiving element (710) is attached to a shaft (706), which is rotatable mounted into a base support member (720), such as a base plate, e.g., by at least one bearing (707). Accordingly, the cup receiving element (710) and the cup (702) can (partially) rotate around axis (712). Such a (partial) rotation is driven by an elastic coupling element (708), such as a spring wire, attached to the shaft (706), for example above or below said bearing (707).

A heating (719), in particular a radiation element, which emits electromagnetic radiation in the wavelength range below 3 µm (3000 nm), more preferably below 1 µm (1000 nm), is placed in close vicinity (preferably not more than 75 mm distance) of the shaft (706) and/or the cup-receiving element (710). Such a radiation element (719) may be, for example, a light emitting diode (preferably having a wavelength range 450-780 nm), a near-IR diode (preferably having a wavelength range 780-1500 nm), or a UV diode (preferably having a wavelength range 300-450 nm). A portion of the emitted energy (indicated by the dotted arrow in FIG. 11) is converted into heat in the shaft (706) and/or in the cup-receiving element (710) by absorption. This energy absorption is dependent on surface properties: the more dark (e.g., black) and the rougher the surface of the shaft (706) and/or the cup-receiving element (710) is/are made, the more radiation can be absorbed. In the theoretical approximation of an ideally "black" body, radiation absorption is independent from the wavelength.

The upper cut-off of the spectral range of emitted radiation (wavelength of 3 µm, preferably 1 µm) is important, because the emitted radiation should not interfere with the spectral range of thermal radiation according to Planck's law. This law describes that thermal radiation is emitted only in the range above 3 µm for an (ideally black) body at a temperature between 30 and 40°. The thermal radiation (as indicated by the dotted arrow in FIG. 11) directed to the shaft (706) and/or the cup-receiving element (710) can then be used to measure the temperature of the shaft (706) and/or the cup-receiving element (710) in a nearby (preferably maximum 75 mm distance) temperature sensor (718). The temperature sensor (718) may be, for example, a (calibrated) photodiode or photoresistor, or a pyro-electric sensor. Usually, these sensors absorb thermal radiation only in a certain spectral range that depends on the temperatures to be measured. In particular, sensors intended to measure temperatures between 20 and 50° C. typically have a spectral sensitivity in the range between 3 µm and 30 µm, because the thermal radiation according to Planck's law on thermal radiation peaks in this range.

For example, a near-IR diode with emission maximum around 850 nm (2 W total power, OSRAM SSH4715AS) was used as a heating (719) and a pyro-electric detector with spectral sensitivity between 5, 5 and 14 µm (MELEXIS MLX 90615) was used as temperature sensor (719). Shaft (706) and cup receiving element (710) were blackened by conventional blackboard color to increase absorption of thermal radiation. Non-movable surrounding metal parts were heated to 37° C. by 2 conventional thermo-resistors (5 W power in total) and controlled to maintain this value by a conventional thermo-regulation consisting of said thermo-resistors and a thermocouple as sensor. The IR diode enabled additional heating of the cup receiving element and the cup from 35.5° C. (as achieved by thermal radiation from the surrounding non-movable parts) to 37° C. (as required to perform a thromboelastometric measurement at typical body temperature) within less than 30 seconds. An alternative radiation source, a light emitting diode with emission maximum at 660 nm (CREE, Xlamp XP, XPEPHR-L 1-0000-00901) and an average output power of 0.35 W, was also able to heat the cup receiving element (710) and cup (702) from 35.5° C. to 37° C. with less than 30 seconds. The maximum achievable temperature difference between surrounding metal parts and cup was about 16° C. for the diode emitting at 850 nm maximum and about 12° C. for the diode emitting at 660 nm maximum.

The invention claimed is:

1. An apparatus for measuring the coagulation characteristics of a blood sample, comprising:
   a cup suitable for receiving the blood sample;
   a cup receiving element providing detachable fixing for the cup in a measurement position;
   a pin suitable to be dipped into said blood sample in said cup, wherein the pin is rotational symmetric, the rotational symmetry axis of the pin forms a vertical axis, and the pin is attached to supporting means in a detachable manner;
   rotating means comprising a shaft, which extends along the vertical axis, which is rotatable around the vertical axis, and which is attached to the cup receiving element or to supporting means for the pin, such that a rotation of the shaft causes a rotation of the cup receiving element or of the supporting means for the pin, and/or vice versa; and
   detection means capable of detecting a rotation around said vertical axis and/or variations in a rotation around said vertical axis;
   wherein the rotating means and the detection means are provided below the cup, the pin, and the cup receiving element, thereby reducing weight load on the pin so as to improve the accuracy of the measuring of coagulation characteristics.

2. The apparatus according to claim 1, wherein the cup receiving element comprises temperature control means to control the temperature of the cup and/or of the blood sample.

3. The apparatus according to claim 1, wherein the shaft is attached to the cup receiving element, such that a rotation of the shaft causes a rotation of the cup receiving element and/or vice versa.

4. The apparatus according to claim 3, wherein the supporting means for the pin are immovable, such that the pin attached to the supporting means is immovable.

5. The apparatus according to claim 3, wherein the supporting means for the pin are a cover.

6. The apparatus according to claim 1, wherein the shaft is attached to supporting means for the pin, such that a rotation of the shaft causes a rotation of the supporting means for the pin, and/or vice versa.

7. The apparatus according to claim 6, wherein the cup receiving element is immovable, such that the cup fixed to the cup receiving element is immovable.

8. The apparatus according to claim 1, wherein the detection means are selected from optical, electrical, or magnetic detection means.

9. The apparatus according to claim 1, wherein the detection means comprise one or more capacitor elements.

10. The apparatus according to claim 9, wherein the capacitor element comprises an electrically non-conductive support and at least one electrically conductive and rotatable layer disposed on the support.

11. The apparatus according to claim 10, wherein the electrically non-conductive support extends essentially perpendicularly to the vertical axis.

12. The apparatus according to claim 10, wherein the at least one electrically conductive and rotatable layer rotates with the same angular amplitude as the shaft.

13. The apparatus according to claim 9, wherein the detection means further comprises an electrical circuit capable of detecting a rotation of at least +/−2° with an accuracy of at least 0.2° on a time frame of at most 5 seconds.

14. The apparatus according to claim 1, wherein the detection means comprises a capacitive detection means for detecting variations in the rotation around the vertical axis caused by blood coagulation, the capacitive detection means comprising:
   a rotatable dielectric element, which is capable of rotating around the vertical axis and which does not have a circular shape with the vertical axis as center;
   two fixed capacitor elements; and
   an electrical circuit;
   wherein each of the two fixed capacitor elements comprises at least one electrically conductive element; the two fixed capacitor elements are arranged such that the electrically conductive elements of the capacitor elements face each other; and the dielectric element is at least partially placed between the two fixed capacitor elements;
   wherein the electrical circuit is capable of detecting a rotation of the rotatable dielectric element around the vertical axis of at least +/−2° with an accuracy of at least 0.2° in a time frame of at most 5 seconds.

15. The apparatus according to claim 14, wherein the electrical circuit is connected to at least one of the two fixed capacitor elements.

16. The apparatus according to claim 1, further comprising a temperature control device for controlling the temperature of the cup and/or of the cup receiving element while measuring the coagulation characteristics of the blood sample, the temperature control device comprising:
- a heater comprising an electromagnetic radiation emitting element emitting radiation with an emission maximum in the wavelength range from 300 to 3,000 nm; and
- a temperature sensing element for contactless measurement of thermal radiation in the wavelength range from more than 3,000 nm to 30,000 nm.

17. The apparatus according to claim 16, wherein the temperature control device comprises a controlling means for activating or deactivating the heater depending on the temperature measured by the temperature sensing element.

18. The apparatus according to claim 1, wherein the rotating means comprise an elastic coupling element, which provides a rotation to the shaft.

19. The apparatus according to claim 18, wherein the elastic coupling element is selected from a spring wire, a piezoelectric bending element, and a field-based forcing element using an electric force or using a magnetic force.

20. The apparatus according to claim 1, wherein the rotating means comprise a bearing.

21. The apparatus according to claim 20, wherein the bearing is disposed in a base support member.

22. The apparatus according to claim 21, wherein the shaft extends through the base support member.

* * * * *